(12) United States Patent
Mullens et al.

(10) Patent No.: US 11,547,988 B2
(45) Date of Patent: Jan. 10, 2023

(54) CATALYTIC COMPOSITION AND STRUCTURES MADE THEREOF

(71) Applicants: VITO NV (VLAAMSE INSTELLING VOOR TECHNOLOGISCH ONDERZOEK NV), Mol (BE); UNIVERSITEIT ANTWERPEN, Antwerp (BE)

(72) Inventors: Steven Mullens, Mol (BE); Lidia Protasova, Mol (BE); Jasper Lefevere, Moorsele (BE)

(73) Assignees: VITO NV (VLAAMSE INSTELLING VOOR TECHNOLOGISCH ONDERZOEK NV), Mol (BE); UNIVERSITEIT ANTWERPEN, Antwerp (BE)

(*) Notice: Subject to any disclaimer, the term of this patent is extended or adjusted under 35 U.S.C. 154(b) by 0 days.

(21) Appl. No.: 17/514,813

(22) Filed: Oct. 29, 2021

(65) Prior Publication Data

US 2022/0048013 A1 Feb. 17, 2022

Related U.S. Application Data

(62) Division of application No. 15/765,212, filed as application No. PCT/EP2016/073443 on Sep. 30, 2016, now Pat. No. 11,192,095.

(30) Foreign Application Priority Data

Sep. 30, 2015 (EP) .................................... 15187788

(51) Int. Cl.
*C07C 1/20* (2006.01)
*B01J 29/40* (2006.01)
(Continued)

(52) U.S. Cl.
CPC .................. *B01J 29/40* (2013.01); *B01J 2/08* (2013.01); *B01J 2/20* (2013.01); *B01J 27/14* (2013.01);
(Continued)

(58) Field of Classification Search
CPC ....... C07C 11/02; C07C 1/20; C07C 2521/08; C07C 2521/16; C07C 2529/40;
(Continued)

(56) References Cited

U.S. PATENT DOCUMENTS 5,518,678 A 5/1996 Miyamoto et al.
6,401,795 B1 6/2002 Cesarano, III et al.
(Continued)

FOREIGN PATENT DOCUMENTS

CN 103827055 A 5/2014
EP 0496226 A1 7/1992
(Continued)

OTHER PUBLICATIONS

International Search Report and Written Opinion from International Application No. PCT/EP2016/073443, dated Dec. 21, 2016.
(Continued)

*Primary Examiner* — Sharon Pregler
(74) *Attorney, Agent, or Firm* — Merchant & Gould P.C.

(57) ABSTRACT

Methods use a catalytic composition built up from a ceramic material including a catalytic material and a first inorganic binder and a second inorganic binder and a catalytic structure made thereof. Preferably, the structure is made by a colloidal ceramic shaping technique. The structure is used for catalytic or ion exchange applications. The catalytic structures have excellent mechanical, physicochemical and catalytic properties.

17 Claims, 6 Drawing Sheets

(51) Int. Cl.
*B01J 29/08* (2006.01)
*B01J 29/70* (2006.01)
*B01J 37/00* (2006.01)
*B28B 1/00* (2006.01)
*B28B 3/20* (2006.01)
*B01J 29/18* (2006.01)
*C10G 3/00* (2006.01)
*B01J 2/08* (2006.01)
*B01J 27/14* (2006.01)
*C04B 35/622* (2006.01)
*B01J 2/20* (2006.01)
*B01J 37/03* (2006.01)
*C04B 38/00* (2006.01)
*C07C 11/02* (2006.01)
*B01J 35/04* (2006.01)
*B01J 35/06* (2006.01)
*B01J 35/08* (2006.01)
*C04B 35/01* (2006.01)
*C04B 111/00* (2006.01)

(52) U.S. Cl.
CPC ............ *B01J 29/084* (2013.01); *B01J 29/18* (2013.01); *B01J 29/7007* (2013.01); *B01J 37/0009* (2013.01); *B01J 37/038* (2013.01); *B28B 1/001* (2013.01); *B28B 3/20* (2013.01); *C04B 35/622* (2013.01); *C04B 38/008* (2013.01); *C07C 1/20* (2013.01); *C07C 11/02* (2013.01); *C10G 3/44* (2013.01); *C10G 3/49* (2013.01); *B01J 35/04* (2013.01); *B01J 35/06* (2013.01); *B01J 35/08* (2013.01); *C04B 35/01* (2013.01); *C04B 2111/0081* (2013.01); *C04B 2111/00181* (2013.01); *C07C 2521/08* (2013.01); *C07C 2521/16* (2013.01); *C07C 2529/40* (2013.01); *C07C 2529/80* (2013.01); *C07C 2529/84* (2013.01); *C10G 2400/20* (2013.01)

(58) Field of Classification Search
CPC .. C07C 2529/80; C07C 2529/84; B01J 27/14; B01J 29/084; B01J 29/18; B01J 29/40; B01J 29/7007; B01J 2/08; B01J 2/20; B01J 35/04; B01J 35/06; B01J 35/08; B01J 37/0009; B01J 37/038; C10G 2400/20; C10G 3/44; C10G 3/49
See application file for complete search history.

(56) References Cited

U.S. PATENT DOCUMENTS

| | | |
|---|---|---|
| 6,993,406 B1 | 1/2006 | Cesarano, III et al. |
| 2003/0006534 A1 | 1/2003 | Taboas et al. |
| 2003/0181322 A1 | 9/2003 | Chang et al. |
| 2011/0129640 A1* | 6/2011 | Beall .................. C04B 35/63492 428/116 |
| 2011/0237426 A1 | 9/2011 | Kikuchi et al. |
| 2014/0065042 A1* | 3/2014 | Andersen .................. B01J 35/04 502/68 |

FOREIGN PATENT DOCUMENTS

| | | |
|---|---|---|
| EP | 0592050 A1 | 4/1994 |
| EP | 2907570 A1 | 8/2015 |
| WO | 2007/019211 A1 | 2/2007 |
| WO | 2009/027525 A2 | 3/2009 |

OTHER PUBLICATIONS

Aranzabal et al., "Optimization of process parameters on the extrusion of honeycomb shaped monolith of H-ZSM-5 zeolite," Chem. Eng. J., 162 (2010) 415-423.

Zamaniyan et al., "Tube fitted bulk monolithic catalyst as novel structured reactor for gas-solid reactions," Appl. Catal. A: Gen., 385 (2010) 214-223.

Lee et al., "Textural Properties and Catalytic Applications of ZSM-5 Monolith Foam for Methanol Conversion," Catal Letters 129 (2009) 408-415.

Guo et al., "Simulation of non-catalytic partial oxidation and scale-up of natural gas reformer," Fuel Process. Technol., 98 (2012) 45-50.

Guo et al., "Comparison among monolithic and randomly packed reactors for the methanol-to-propylene process," Chem. Eng. J., 207-208 (2012) 734-745.

Freiding et al., "Extrusion of zeolites: Properties of catalysts with a novel aluminium phosphate sintermatrix," Appl. Catal. A: Gen., 328 (2007) 210-218.

Couck et al., "$CO_2$, $CH_4$ and $N_2$ separation with a 3DFD-printed ZSM-5 monolith," Chem. Eng. J., 308 (2017) 719-726.

Rao et al., "Microfabricated Deposition Nozzles for Direct-Write Assembly of Three-Dimensional Periodic Structures," Adv. Mater., 17, No. 3 (Feb. 10, 2005) 289-293.

Chinese Office Action for Chinese Patent Application No. 201680057232.8 dated Jan. 4, 2020 (18 pages).

Chinese Office Action for Chinese Patent Application No. 201680057232.8 dated Jan. 4, 2021 (English translation, 17 pages).

Hargreaves et al., "A Survey of the Influence of Binders in Zeolite Catalysis", Catalysis Science & Technology, 2013, pp. 1165-1171, vol. 3, RSC Publishing.

Lee et al., "Influence of Catalyst Binders on the Acidity and Catalytic Performance of HZMS-5 Zeolites for Methanol To-Propylene (MTP) Process: Single and Binary Binder System", Top. Catal., 2010, pp. 247-253, vol. 53.

Yao, et al., "Select of Molding Formulations of Honeycomb SCR DeNOx Catalysts", China Environmental Science, 2013, pp. 2148-2156, vol. 33, No. 12.

Lefevere et al. "The benefit of design of support architectures for zeolite coated structures catalysts for methanol-to-olefin conversion." Catalysis Today, vol. 216 (2013) pp. 18-23.

* cited by examiner

CATALYTIC COMPOSITION AND STRUCTURES MADE THEREOF

CROSS-REFERENCE TO RELATED APPLICATIONS

This application is a Divisional of U.S. application Ser. No. 15/765,212, filed 30 Mar. 2018, which is a National Stage Application of PCT/EP2016/073443, filed 30 Sep. 2016, which claims benefit of Serial No. 15187788.3, filed 30 Sep. 2015 in Europe and which applications are incorporated herein by reference. To the extent appropriate, a claim of priority is made to each of the above-disclosed applications.

FIELD OF THE INVENTION

The present invention relates to a catalytic composition, catalytic structures made thereof and the use thereof.

More particularly, the present invention relates to (inherent) catalytic structures having excellent mechanical, physicochemical and catalytic properties, and the use thereof.

BACKGROUND

In industry, catalysts are commonly used in the form of packed bed pellets, however, these pellets can suffer from mass and heat transfer limitations. In order to reduce these limitations, the size of the pellets can be reduced, though this will increase the (unwanted) pressure drop over the catalyst bed.

In the art, structured macroporous catalysts have been investigated combining an inert structured support material, such as foam or honeycombs, with a thin active catalytic coating. In general, such a thin coating of catalytic material applied on the surface of inert supports offers significantly lower pressure drops and shows good mass and heat transfer properties. However, one major drawback of these conventional macroporous structured catalysts is the limited amount of catalyst per reactor volume.

An interesting alternative is a bulk or inherent catalytic structure, also called self-supporting monolithic catalyst, where the active catalytic component is incorporated into the monolith structure. In this way, less volume in the reactor is lost by inert support material. To the contrary, by using self-supporting monolithic catalysts, a high amount of catalytic material can be uniformly introduced in the reactor.

Various methods are available in the art for the synthesis of monolithic structures, however, not all of them can be applied for the synthesis of bulk catalytic structures as the final catalytic structure needs to have high porosity for a good accessibility of the active catalytic sites.

The most commonly used method to shape catalytic monoliths is extrusion. A direct extrusion of zeolitic monoliths containing slurry has already been described in the art, for example by Aranzabal et. al. (Chem. Eng. J. 162 (2010) 415) and Zamaniyan et. al. (Appl. Catal. A Gen. 385 (2010) 214), as one way of manufacturing a self-supporting zeolite honeycomb. Other methods, such as the template method for foam formation, can also be used (Y.-J. Lee et al. Catal. Letters 129 (2009) 408).

Although the methods and self-supporting monolithic catalysts already known in the art aim at overcoming disadvantages of more conventional (coated) catalytic structures, a drawback is that these structures still show limited mass and heat transfer properties in highly exothermic reactions such as methanol-to-olefins (MTO) reactions.

Moreover, modeling studies have suggested that the thickness of the walls and the porosity of the structure will have an impact on the selectivity in this type of reaction (W. Guo et al. Fuel Process. Technol. (2012) 6 and W. Guo et al. Chem. Eng. J. 207-208 (2012) 734).

Furthermore, next to the requirement of being sufficiently porous, bulk catalytic structures also need to have a good mechanical strength. However, the bulk catalytic structures already known in the art often have the problem that either their porosity or their mechanical strength is low.

US 2011/0237426 discloses a manufacturing method of a zeolite structure comprising a mixing step of mixing a plurality of zeolite particles with an inorganic binding material and an organic binder, to prepare a zeolite raw material; a forming step of extruding the zeolite raw material to obtain a formed zeolite article; and a firing step of firing the formed zeolite article to prepare a zeolite structure. The inorganic binding material used in this document contains one class of inorganic binders, i.e. the inorganic binding material contains at least one type of silica sol selected from the group consisting of acid silica sol, silica sol containing silica particles coated with alumina, cationic silica sol, silica sol containing string-like silica particles, and silica sol containing silica particles having a shape where a plurality of spherical silica particles are tied one to the next. It is also disclosed that in the zeolite raw material, the content ratio of the organic binder with respect to the total of the zeolite particles and the inorganic binding material should not be too low, as the viscosity of the formed zeolite article would become too high, and the formed zeolite article cannot be extrusion-formed. Neither should said content ratio of the organic binder be too high, as the porosity of the zeolite structure would become high, and the strength of the structure would lower. Furthermore, the zeolite raw material prepared in the above mixing step is extruded in a predetermined shape, for example a film-like shape, a plate-like shape, a tubular shape, or a honeycomb shape. It is reported that extruding the zeolite structure having a honeycomb shape has a lower pressure drop compared to a honeycomb (which is made of e.g. ceramic material such as cordierite) onto which a catalyst is washcoated. Furthermore, more catalysts can be loaded onto the zeolite structure. It is described that with the disclosed method a zeolite structure having an excellent mechanical strength can be manufactured, however, an outer peripheral wall is preferably disposed to surround the whole outer periphery of the extruded honeycomb zeolite structure to avoid breakdown of this structure.

Despite efforts already made in the art, there is still a need for providing porous, (inherent) catalytic structures having improved mechanical as well as catalytic properties.

SUMMARY OF THE INVENTION

Aspects of the present invention envisage providing an improved catalytic composition and (inherent) catalytic structure made thereof, which overcomes the disadvantages of prior art catalytic structures.

Aspects of the present invention therefore envisage providing such catalytic composition and (inherent) catalytic structure made thereof, having improved mechanical and physicochemical properties compared to prior art catalytic structures.

Aspects of the present invention envisage providing such catalytic composition and (inherent) catalytic structure made thereof, having improved mechanical and catalytic properties (i.e. improved effectiveness of the active catalytic component in the structure) compared to prior art catalytic structures.

According to aspects of the invention, there is therefore provided a method of building (or manufacturing) a (inherent or bulk) catalytic structure. The method comprises shaping a composition to obtain a green structure. The composition, which can be a dry composition, such as a powder, or a (extrudable) slurry, suspension or paste, comprises a ceramic material. The ceramic material comprises a catalytic material and a first and a second inorganic binder. The green structure, which optionally can be dried to impart initial strength, is fired to obtain the bulk catalytic structure.

According to another aspect of the invention, there is provided a bulk or inherent catalytic structure. The bulk catalytic structure is one which can be obtained through the method described in the preceding paragraph.

According to one aspect, the bulk catalytic structure consists of inorganic compounds. The bulk catalytic structure advantageously does not comprise organic compounds.

According to another aspect, the bulk catalytic structure is monolithic and comprises first channels having a length extending in a flow direction and second channels having a length extending in a radial direction. The flow direction and the radial direction are advantageously orthogonal directions. The radial direction can be any direction, even an arcuate direction arranged in a plane transverse to, and advantageously orthogonal to the flow direction. The first channels and the second channels are fluidly connected.

Advantageously, the bulk catalytic structure comprises fibers forming a layered network resulting in the bulk catalytic structure. The fibers, which may have a diameter ranging between 0.1 mm and 2 mm, are advantageously arranged in layers and extend alongside the first and/or the second channels. The fibers within a layer are advantageously spaced apart to form the channels between consecutive fibers. Fibers of consecutive layers advantageously have axes oriented oblique to one another, advantageously at an angle between 30° to 150°, advantageously at an angle between 45° to 135°, advantageously at an angle between 60° to 120°. The layered network advantageously is a periodic structure obtained by stacking identical ones of a repeating stack of layers. The repeating stack can comprise multiple layers with fibers oriented along mutually oblique directions. When fibers of successive layers are disposed mutually orthogonal, a repeating stack comprising alternate layers is obtained. Successive ones of each alternate layer can have their fibers aligned. In this case, the repeating stack consists of two layers and the structure will have straight channels in the direction of stacking. Alternatively, successive ones of at least one of the two alternate layers can be disposed such that the fibers are staggered between the successive ones of the alternate layer. In this case, zigzag channels can be obtained in the direction of stacking. Yet alternatively, or additionally, the porosity between the fibers throughout the catalyst structure changes gradually, obtaining a so-called gradient structure. Yet another alternative is to turn subsequent layers by a few degrees compared to the previous one, obtaining a so-called rotating structure with helix like channels.

Bulk catalytic structures according to the above aspects, and in particular the interconnected first and second channels, feature a more open and hence accessible structure, resulting in a lower pressure drop through the reactor. As a result, the flux of reagents through the reactor is increased, resulting in a higher conversion per mass amount of catalyst. Furthermore, the more open structure improves the heat transfer between the flux of reagents and the catalytic structure (through which the flux of reagents is diffusing or passing) thereby avoiding the formation of hot spots throughout the structure, which in turn minimizes side reactions like coking. In addition, with the above methods, the geometry of the bulk catalytic structures can be better controlled, such that a more uniform geometry is obtained. This enables a uniform flow of reagents through the catalytic structure, thereby avoiding local density differences which may lead to temperature differences and side reactions, in turn resulting in lower selectivity. Bulk catalytic structures according to present aspects therefore are advantageous for use in reactions in which heat and/or mass transport limitations are important (e.g. highly exothermic reactions).

Combining two types of inorganic binders in the catalyst structures according to aspects of the invention provides a synergic effect, i.e. a combinational effect of the use of two different binders and their mutual interaction in the catalyst structures, being beneficial to achieve desired properties in the final structure. More particularly, combining two types of inorganic binders in one catalyst structure, as described in the present invention, has a beneficial impact on the behavior of the material during manufacturing as well as on mechanical and physico-chemical properties, such as mechanical strength, stability, porosity, specific surface area and acidity, of the final structure.

The catalytic structures according to aspects of the invention thus improve mass and heat transfer properties, and hence improve the activity, selectivity and stability of the catalysts, compared to prior art catalytic structures.

According to other aspects of the invention, there is provided the use of the structure of the invention.

Aspects of the invention can be used in catalytic or ion exchange applications as well as in other applications, where high mass and/or heat transfer properties, mixing efficiency (e.g. gas/liquid or liquid/liquid systems), and/or lower pressure drop are required.

In the present invention, the impact (synergic effect) of using two different types of inorganic binders on the stability and selectivity of ZSM-5 structured catalysts in conversion of methanol to olefins was shown. The effect of mass and heat transfer properties of catalytic systems according to aspects of the invention on the stability and selectivity of the methanol-to-olefins reaction was demonstrated. Optimization of the macroscopic structure of the catalyst according to aspects of the invention leads to improvement of the selectivity and stability of the catalytic process.

Advantageous aspects of the present invention are set out herein.

BRIEF DESCRIPTION OF THE DRAWINGS

Aspects of the invention will be described in more detail with reference to the appended drawings.

DETAILED DESCRIPTION OF THE INVENTION

Figure 1:
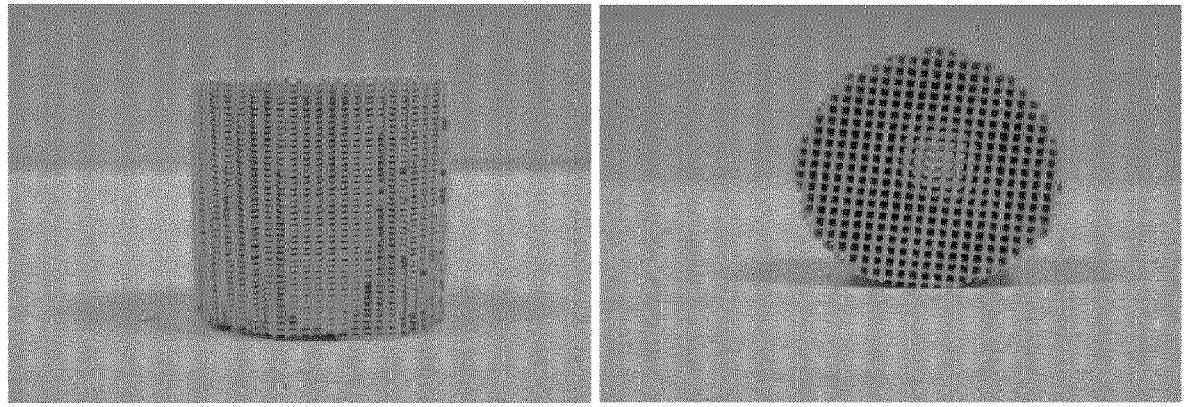
FIG. 1 is a picture of a 3DFD structure of an embodiment of the invention with straight channels (1-1 structure).

According to an aspect of the invention, there is provided a catalytic composition and (inherent) catalytic structure made thereof.

In the context of the present invention, an inherent catalytic structure, also called bulk catalytic structure or self-supporting monolithic catalyst, refers to a catalytic structure where the active catalytic component is incorporated into (or inside) the (monolith) structure.

In the context of the present invention, a binary binder bound catalytic structure refers to a (inherent) catalytic structure according to the invention built up from catalytic material and (a combination of) two (different types of) inorganic binders (i.e. a first and second inorganic binder). In the present description, a binary binder bound catalytic structure is also called binary binder structure, binary binder system, or binary binder catalyst.

In one aspect of the invention, the catalytic composition comprises a ceramic material, wherein the ceramic material comprises (or consists of) a catalytic material and a first and second inorganic binder (i.e. (a combination of) two (different types of) inorganic binders).

In another aspect of the invention, a catalytic structure comprises the catalytic composition of the invention. Advantageously, a (inherent) catalytic structure is built up from the catalytic composition of the invention.

The (inherent) catalytic structure of the invention is built up from (or made of) a ceramic material which comprises (or consists of) a catalytic material and a first and second inorganic binder (i.e. (a combination of) two (different types of) inorganic binders).

In other words, the (inherent) catalytic structure of the invention is built up from (or made of) a ceramic material, said ceramic material comprising (or consisting of) a catalytic material and a first and second inorganic binder (i.e. (a combination of) two (different types of) inorganic binders). The first and second inorganic binders may form a binary binder composition.

More particularly, the active catalytic component (of the catalytic material), together with the first and second inorganic binder, is incorporated (or manufactured) into (or inside) the catalytic (monolith) structure of the invention.

Advantageously, the first and second inorganic binder are added to the catalytic material for shaping the (inherent) catalytic structure of the invention.

By adding the first and second inorganic binder to the catalytic material (or by building up the structure with catalytic material together with the first and second inorganic binder), the formed (inherent) catalytic structure of the invention has sufficient or even improved mechanical properties (compared to prior art catalytic structures). In addition, its catalytic properties, i.e. the activity of the active catalytic component in the structure, is improved (compared to prior art catalytic structures).

In the context of the present invention, a catalyst or catalytic material refers to a material having (exhibiting) catalytic activity (with respect to a chemical reaction under consideration).

In the context of the present invention, an inherent catalytic material refers to a material inherently (or intrinsically) having (exhibiting) catalytic activity (such as a zeolite material).

Advantageously, the catalytic material of the composition of the present invention comprises (or is made of or consists of) an inorganic compound.

More advantageously, the catalytic material comprises (or consists of) (particles of) zeolites (zeolite material, zeolite particles, zeolite powder), alumina (alumina particles), activated alumina, silica (silica particles), silica gel, zirconia, ceria (i.e. CeO$_2$, also known as cerium (IV) oxide, ceric oxide, cerium oxide, or cerium dioxide), mixed metal oxides, activated carbon, carbon molecular sieves, (particles having) metal-organic frameworks (MOF), or polyoxometalate (POM).

In the context of the present description, 'mixed metal oxides' refer to a single homogeneous composition comprising several kinds of metal oxides, the term being commonly used in the art.

In the context of the present description, 'metal-organic frameworks' refer to compounds consisting of metal ions or clusters coordinated to organic ligands to form one-, two-, or three-dimensional structures, the term being commonly used in the art.

Even more advantageously, the catalytic material comprises (or consists of) zeolites (zeolite material, zeolite particles, zeolite powder), alumina (alumina particles), or silica (silica particles).

Most advantageously, the catalytic material of the composition of the present invention comprises (or consists of) zeolites (or zeolite material, zeolite particles, zeolite powder).

In the composition of the present invention, the zeolites can be made of at least one type of zeolite selected from the group consisting of ZSM-5 type zeolite, β-type zeolite, Y-type zeolite, mordenite type zeolite, and ferrierite type zeolite. Among these types of zeolite, ZSM-5 type zeolite, β-type zeolite and the like are preferable.

In an embodiment of the invention using three-dimensional fiber deposition for building up the catalytic structure, the catalytic material of the composition is preferably made of ZSM-5 type zeolite.

Finding suitable sizes of the particles for use as catalytic material in the composition of the present invention depends on the used (colloidal ceramic) shaping technique and is well within the practice of those skilled in the art.

In an embodiment of the invention, in particular when using three-dimensional fiber deposition for building up the catalytic structure, the size of the zeolite particles is comprised between 1 µm and 40 µm.

In the context of the present invention, an inorganic binder refers to an inorganic binding material which permanently binds the particles of the catalytic material to one another, or which forms other (crystalline) phases during drying or firing.

Advantageously, the total amount of (the two) inorganic binders (i.e. total amount of the first and second inorganic binder) in the catalytic material of the composition of the present invention is comprised between 10 wt % and 50 wt %.

More advantageously, the ratio of the (amount of) catalytic material to the (total amount of the two) inorganic binders in the composition of the present invention is between 85 wt % catalytic material to 15 wt % inorganic binders and 65 wt % catalytic material to 35 wt % inorganic binders, such as 75 wt % catalytic material to 25 wt % inorganic binders.

In the context of the present invention, wt % refers to the percentage of the component under consideration by total solid weight of the formed catalytic structure (i.e. total weight of the catalytic composition including the catalytic material and the inorganic binders).

Advantageously, in the composition of the present invention, the first inorganic binder is selected from a first class of inorganic binders and the second inorganic binder is selected from a second class of inorganic binders. In other words, the first inorganic binder selected from a first class of inorganic binders is combined (or used together) with the second inorganic binder selected from a second class of inorganic binders.

More advantageously, the first class of inorganic binders comprises (or consists of) a clay binder, and the second class of inorganic binders comprises (or consists of) colloidal silica, colloidal alumina, colloidal zirconia, colloidal yttrium oxide, or colloidal tin oxide.

The first class of inorganic binders can be a clay binder, and the second class of inorganic binders can be a colloid in which inorganic particles, such as silica, alumina, zirconia, etc. are suspended.

Even more advantageously, said clay binder comprises (or consists of) bentonite, sodium bentonite, calcium bentonite, potassium bentonite, kaolinite, montmorillonite-smectite, illite, chlorite, or attapulgite.

More advantageously, the first class of inorganic binders comprises (or consists of) bentonite, sodium bentonite, calcium bentonite, potassium bentonite, kaolinite, montmorillonite-smectite, illite, chlorite, or attapulgite; and the second class of inorganic binders comprises (or consists of) colloidal silica, colloidal alumina, colloidal zirconia, colloidal yttrium oxide, or colloidal tin oxide.

More particularly, a first inorganic binder selected from any of the inorganic binders of the first class can be combined (or used together) with a second inorganic binder selected from any of the inorganic binders of the second class.

More specifically, the first inorganic binder is selected from the group consisting of bentonite, sodium bentonite, calcium bentonite, potassium bentonite, kaolinite, montmorillonite-smectite, illite, chlorite, and attapulgite (a first class of inorganic binders); and the second inorganic binder is selected from the group consisting of colloidal silica, colloidal alumina, colloidal zirconia, colloidal yttrium oxide, and colloidal tin oxide (a second class of inorganic binders).

Even more advantageously, the first inorganic binder is bentonite and the second inorganic binder is colloidal silica.

Advantageously, in the composition of the present invention, the first inorganic binder is selected from a first class of inorganic binders and the second inorganic binder is selected from a third class of inorganic binders. In other words, the first inorganic binder selected from the first class of inorganic binders is combined (or used together) with the second inorganic binder selected from a third class of inorganic binders.

The first class of inorganic binders can be a clay binder, and the third class of inorganic binders can comprise an inorganic thermohardening compound, e.g. present in solution, such as aluminium phosphate.

More advantageously, the first class of inorganic binders comprises (or consists of) bentonite, sodium bentonite, calcium bentonite, potassium bentonite, kaolinite, montmorillonite-smectite, illite, chlorite, or attapulgite; and the third class of inorganic binders comprises (or consists of) aluminiumphosphate, magnesium-chromium phosphate, aluminum-chromium phosphate, or zinc phosphate.

More particularly, a first inorganic binder selected from any of the inorganic binders of the first class can be combined (or used together) with a second inorganic binder selected from any of the inorganic binders of the third class.

More specifically, the first inorganic binder is selected from the group consisting of bentonite, sodium bentonite, calcium bentonite, potassium bentonite, kaolinite, montmorillonite-smectite, illite, chlorite, and attapulgite (a first class of inorganic binders); and the second inorganic binder is selected from the group consisting of aluminiumphosphate, magnesium-chromium phosphate, aluminum-chromium phosphate, and zinc phosphate (a third class of inorganic binders).

Even more advantageously, the first inorganic binder is bentonite and the second inorganic binder is aluminium phosphate.

Throughout the present description, aluminiumphosphate refers to monoaluminium phosphate and is denoted as $AlPO_4$.

Advantageously, in the composition of the present invention, the first inorganic binder is selected from a second class of inorganic binders and the second inorganic binder is selected from a third class of inorganic binders. In other words, the first inorganic binder selected from the second class of inorganic binders is combined (or used together) with the second inorganic binder selected from the third class of inorganic binders.

The second class of inorganic binders can be a colloid in which inorganic particles, such as silica, alumina, zirconia, etc. are suspended, and the third class of inorganic binders can comprise an inorganic thermohardening compound, e.g. present in solution, such as aluminium phosphate.

More advantageously, the second class of inorganic binders comprises (or consists of) colloidal silica, colloidal alumina, colloidal zirconia, colloidal yttrium oxide, or colloidal tin oxide; and the third class of inorganic binders comprises (or consists of) aluminiumphosphate, magnesium-chromium phosphate, aluminum-chromium phosphate, or zinc phosphate.

More particularly, a first inorganic binder selected from any of the inorganic binders of the second class can be combined (or used together) with a second inorganic binder selected from any of the inorganic binders of the third class.

More specifically, the first inorganic binder is selected from the group consisting of colloidal silica, colloidal alumina, colloidal zirconia, colloidal yttrium oxide (a second class of inorganic binders), and colloidal tin oxide; and the second inorganic binder is selected from the group consisting of aluminiumphosphate, magnesium-chromium phosphate, aluminum-chromium phosphate, and zinc phosphate (a third class of inorganic binders).

Even more advantageously, the first inorganic binder is colloidal silica and the second inorganic binder is aluminiumphosphate.

According to an aspect of the invention, an (inherent or bulk) catalytic structure is made starting from the catalytic composition as indicated above. The catalytic composition is shaped to obtain a green structure as described below. A three dimensional printing technique is advantageously used for shaping. The three dimensional printing technique can be based on a powder or on a viscous paste. The green structure, which is optionally dried, is fired (i.e. is subjected to a thermal treatment) to obtain the catalytic structure.

Advantageously, the structure of the present invention is made by a colloidal ceramic shaping technique. In the context of the present invention, "a colloidal ceramic shaping technique" refers to a shaping technology involving the preparation of a suspension, slurry, or paste of the catalytic material and (together with) the first and second inorganic binder; and shaping the suspension, slurry, or paste into the structure according to the invention.

More advantageously, in an embodiment of the invention, the structure of the present invention is made (or fabricated, manufactured, built) by (or utilizing) three-dimensional fiber deposition (3DFD).

A three-dimensional (inherent) catalytic structure according to such an embodiment of the present invention comprises (or consists of, or is built up from) fibers made of a catalytic material and a first and second inorganic binder (i.e. (a combination of) two (different types of) inorganic binders).

Three-dimensional (3D) fiber deposition refers to a 3D-printing technique, also referred to as robocasting technique (or robocasting manufacturing method). Robocasting technique is an extrusion-based robotic deposition known in the art, as for instance disclosed in U.S. Pat. No. 6,401,795.

Advantageously, by utilizing three-dimensional fiber deposition in an embodiment of the invention, the structure is built up layer-by-layer, forming a network between the fibers of the structure according to a (pre-determined) three-dimensional pattern (or form, shape, architecture). As such, using three-dimensional fiber deposition, a periodic structure is obtained.

By adding the first and second inorganic binder to the catalytic material (or by building up the structure with fibers of catalytic material together with the first and second inorganic binder) in an embodiment of the invention, the robocasted (three-dimensional) (inherent) catalytic structure (or robocasted monolith) has sufficient or even improved mechanical properties and improved physicochemical properties (compared to prior art catalytic structures). Moreover, it has been found that the robocasted structure in an embodiment of the invention has sufficient or even improved mechanical properties and that its catalytic properties, i.e. the activity of the active catalytic component in the structure, is improved (compared to prior art catalytic structures).

In the 3D fiber deposition or robocasting manufacturing method used in an embodiment of the present invention for fabricating a three-dimensional (inherent) catalytic structure, the added inorganic binders are so-called permanent inorganic binders. During the 3D fiber deposition or robocasting manufacturing method, also temporary organic additives (such as methylcellulose) can be added to modify the rheology (flow behavior) of the extrudate. More particularly, temporary organic additives can be added to improve the forming properties or shape retention properties of the formed 3D (inherent) catalytic structure, after which the organic additives are removed from the formed structure.

Suitable organic additives for use in a 3D fiber deposition or robocasting manufacturing method in an embodiment of the invention for fabricating a three-dimensional (inherent) catalytic structure will be apparent for those skilled in the art.

Finding suitable concentrations of organic additive for use in the 3D fiber deposition or robocasting manufacturing method in an embodiment of the invention for fabricating a three-dimensional (inherent) catalytic structure depends on the type of inorganic binders used as well as on the type of organic additive used and will be apparent for those skilled in the art.

The architecture of the structure of the present invention is a periodic structure, advantageously a periodic 3D-printed structure. Such a periodic structure can be formed of a repeating stack of layers. The repeating stack can consist of two, three, four or more layers. Each layer advantageously comprises a plurality of fibers, possibly arranged parallel to one another and spaced apart within the layer. Fibers of consecutive layers in the repeating stack can be arranged oblique to one another, such as having axes oriented at an angle between 30° to 150°, or at an angle between 60° and 120° relative to one another, or e.g. having axes being perpendicular to one another. By spacing the fibers apart, channels are formed. When fibers are straight, the channels within a layer will be straight as well. When fibers follow an arcuate path, the channels within a layer will be tortuous. By adequate stacking of the layers in the repeating stack, channels oriented along a direction of stacking can be formed. These latter channels can be straight, or present a tortuosity.

Advantageously, the architecture of the structure is a structure with straight channels, a zigzag channel structure, a gradient structure, a rotating structure. Advantageously, the architecture of the structure is a structure with straight channels or with zigzag channels.

In the context of the present invention, a structure with straight channels refers to a structure with straight channels in both directions: flow and radial. In the present description such a structure is denoted as a 1-1 structure.

In the context of the present invention, a structure with zigzag channels (i.e. a tortuous path) in flow direction and straight channels in radial direction is denoted as a 1-3 structure.

In the context of the present invention, a gradient structure refers to a 3D structure with more or less catalyst at the wall, center, top, and/or bottom of the catalyst bed.

In the context of the present invention, a rotating structure refers to a 3D structure with helix like channels, or shifted helix like channels.

Advantageously, by building up the structure of the present invention by a colloidal ceramic shaping technique, a (macro)porous (3D) (inherent) catalytic structure (or robocasted monolith) is obtained and the accessibility of the catalyst is enhanced (compared to prior art catalytic structures).

The pore size of the macropores of the structures of the invention depends on the used (colloidal ceramic) shaping technique, the catalytic material used, the type of the two inorganic binders used, and the architecture of the catalytic structure.

More advantageously, the ceramic material (comprising or consisting of catalytic material) building up the catalytic structure of the present invention is (made) porous.

Suitable methods for making the ceramic material porous will be apparent for those skilled in the art.

More advantageously, by building up the structure by three-dimensional fiber deposition in an embodiment of the invention, a robocasted (macro)porous 3D (inherent) catalytic structure (or robocasted monolith) is obtained and the accessibility of the catalyst is enhanced (compared to prior art catalytic structures). A 3DFD structure of an embodiment of the invention with straight channels (1-1 structure) is shown in FIG. 1. In the context of 3DFD, the term macroporous refers to the porosity of the robocasted structure with macropores having a pore size greater than 50 μm in diameter.

Even more advantageously, the fibers of the (3DFD) robocasted structure in an embodiment of the present invention are (made) porous.

More particularly, in an embodiment of the invention the structure is built up from porous fibers (by 3DFD). By making the fibers of the structure porous, the accessibility of the catalyst is even more enhanced (compared to prior art catalytic structures).

More advantageously, the fibers of the (3DFD) robocasted structure in an embodiment of the present invention are made porous utilizing (by) phase inversion.

The term phase inversion is known in the art of producing porous constructs, as for instance defined in the textbook entitled "Basic Principles of membrane Technology", from Mulder M., Kluwer Academic Publishers, 1996.

WO 2009/027525, for example, describes a method for producing a three-dimensional macroporous filament construct based on phase inversion and construct thereby obtained.

It has been found that the robocasted (macro)porous (inherent) catalytic structure (or robocasted monolith) in an embodiment of the invention built up from fibers made of a catalytic material and (a combination of) two (different types of) inorganic binders with a ratio of 85% catalytic material to 15% inorganic binders, more preferably a ratio of 75% catalytic material to 25% inorganic binders, even more preferably a ratio of 65% catalytic material to 35% inorganic binders, has sufficient or even improved mechanical properties (compared to prior art catalytic structures). Moreover, it has been found that such structure of the invention has improved mechanical properties and that its catalytic properties are improved (compared to prior art catalytic structures).

Advantageously, the structure of the present invention comprises a (at least one) further catalytic component, different from the catalytic material of the ceramic material.

More particularly, the material of the further catalytic component is different from the catalytic material of the ceramic material building up the structure.

According to an aspect of the present invention, the structure of the present invention can be used for catalytic applications or ion exchange applications.

Advantageously, the structure of the present invention is used for catalytic applications.

More advantageously, the structure of the present invention is used for methanol-to-olefins reactions.

The present invention is further illustrated by means of the following examples.

EXAMPLES

In the examples described below, robocasting is used as colloidal ceramic shaping technique for obtaining the catalytic structures.

Robocasting technique is an extrusion-based robotic deposition known in the art. Performing a robocasting manufacturing method (or three-dimensional (3D) fiber deposition) for obtaining a robocasted (macro)porous 3D (inherent) catalytic structure (or robocasted monolith) is well within the practice of those skilled in the art.

In example 1 described below, robocasted three-dimensional (inherent) catalytic structures (having the same 1-1 structure) are prepared based on zeolite ZSM-5 powder as the (first) active catalytic material having different combinations of first and second inorganic binders added thereto, for fabricating the fibers of (or constituting) the robocasted structure. Also structures using only one single inorganic binder were analyzed as comparative examples.

The catalytic results of robocasted ZSM-5 structures applied in the conversion of methanol to olefins (methanol-to-olefin reaction) are described in example 2. The impact of different combinations of first and second inorganic binders on the catalytic properties was investigated. The influence of the architecture on the selectivity and stability of the catalysts is also demonstrated for two different architectures of the robocasted silica/aluminiumphosphate binary binder catalyst of the invention.

Other suitable (first) active catalytic materials and other combinations of two different types of inorganic binders used for forming a robocasted (three-dimensional) (inherent) catalytic structure of the invention, as well as other suitable architectures of the structures and use of the formed structures in other types of reactions, will be apparent for those skilled in the art from the present description.

Other types of catalytic reactions can for example include reactions with mass and heat transfer limitations, highly exo- and endothermic reactions, reactions with a problem of catalyst support stability and/or sensitive in respect to safety. More particularly, other types of catalytic reactions can for example be the Sabatier reaction (methanation of carbon dioxide by $CO_2+4H_2 \rightarrow CH_4+2H_2O$), or the nitrogen oxide decomposition reaction ($2N_2O \rightarrow 2N_2+O_2$).

Example 1:

1A. Preparation of Robocasted (Macro)Porous 3D (Inherent) Catalytic Structures

As catalytic material, zeolite ZSM-5 powder with a Si/Al ratio of 25 was provided by Süd-Chemie (particle size distribution 0.5-22 μm, $d_{50}$ 8 μm). The zeolite powder was used as received.

Bentonite (VWR), colloidal silica (Ludox HS-40, Sigma Aldrich), or aluminiumphosphate solution (Litopix P-1, Zschimmer and Schwartz) were used as first and/or second permanent inorganic binders.

Before use, bentonite was milled with water. Colloidal silica and aluminiumphosphate are milled using 15 mm zirconia balls at 250 rpm for 45 minutes in order to achieve the right particle size distribution ($d_{50}<10$ μm).

After mixing of the binders with water, thereby forming a suspension, zeolite was added to the suspension and mixed using a planetary centrifugal mixer for 2 minutes at 1900 rpm. Depending on the type of binder(s) used, the water content varied between 37% and 65% of the solid weight content in order to achieve good flow behavior of the obtained zeolite/binder paste. As the slurry temperature increased due to vigorously mixing, the viscous paste was cooled to room temperature before extrusion, to prevent water evaporation and changes in paste composition. In case of double binder systems, the binder ratio of the different binders was 50/50. In both single and double binder(s) systems, the ratio of zeolite to total amount of inorganic binder(s) was 65 wt % zeolite/35 wt % binder.

As known in the art, the extrusion behavior of the paste is dependent on the rheology. A shear thinning effect of the extrudate is required for good flow behavior during extrusion and sufficiently high viscosity is necessary to avoid collapse of the structure during and after extrusion. Furthermore, the temperature and humidity are important for the extrusion in order to control the drying of the structure during the robocasting process.

Methylcellulose (Acros Organics) was used as temporary organic additive to modify the rheology of the paste (or extrudate, or extrusion paste), in case the obtained pastes show low viscosity at low shear rates. No extra organic additive was added to the extrudates with bentonite binder, whereas for the other extrusion pastes 0.5 wt % to 1 wt % methylcellulose (Acros Organics) is used to achieve a shear thinning behavior of the paste suitable for robocasting.

Finding suitable concentrations of organic additive for use in the robocasting method depends on the type of organic additive used and is well within the practice of those skilled in the art. For example, a methylcellulose concentration of 0.5 wt % for the silica binder and 1 wt % for the aluminiumphosphate binder resulted in paste with an optimal extrusion behavior.

The robocasting of the structure was performed using a thin 0.9 mm nozzle mounted on a computer numerical controlled machine (CNC). For the extrusion process, the size of the (binder and catalytic material) particles in the paste should be at least an order of magnitude smaller than the width of the nozzle. In order to achieve good flow properties, an extra milling step is performed in case the particle size of the binder and/or the catalytic material is higher than the width of the nozzle used.

Figure 2:
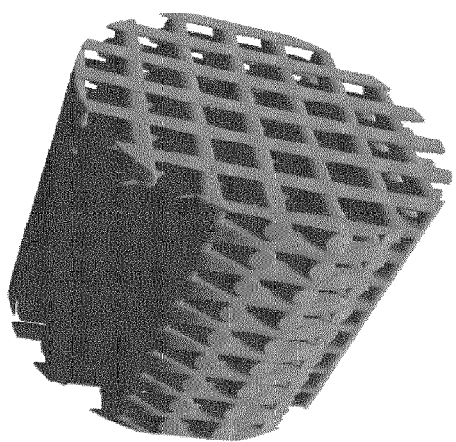
FIG. 2 is a 3D-CT scan image of robocasted binary binder bentonite/silica catalytic structure of the invention.

By continuous extrusion of the paste through the nozzle and programmed movement of the CNC machine in X, Y and Z direction (i.e. the robocasting step), the structure is built up layer-by-layer. The paste is extruded through a single nozzle as a continuous filament forming a fiber. As shown in FIG. 2, a plurality of fibers are arranged side by side at a spaced apart distance within each layer. The orientation of the (axes of the) fibers is changed between consecutive layers to obtain a highly porous structure with channels extending in a radial direction (direction of the fiber axes) and with channels extending in a flow direction (i.e. the direction of stacking of the layers). The periodic structure in FIG. 2 consists of a repeating stack of two layers. However, other structures can easily be conceived.

Key elements in building up the structure layer-by-layer are the volumetric flow of the extrudate and the speed of movement of the nozzle.

As the speed of the nozzle is determined by the CNC machine, the speed of extrusion is adjusted according to the diameter of the nozzle. Finding a suitable flow of the extrudate is well within the practice of those skilled in the art. In case of the 0.9 mm nozzle, the flow was kept at 600 µl/min.

The paste is extruded through a single nozzle as a continuous filament using a constant displacement of the plunger in the paste reservoir in order to achieve homogeneous volumetric flow rate. The extrusion temperature was kept at 20° C. and the relative humidity (RH) was 70%.

The open porosity between the fibres can range between 55% to 95%, advantageously between 65% to 95%, advantageously between 65% and 80%.

The structures were synthesized with an open porosity between the fibres of 68%, not taking into account the internal porosity of the structure (solid material).

The samples were dried after robocasting for achieving a defect-free self-supporting catalyst structure (thereby avoiding collapse of the different layers).

Finding suitable drying methods for use in the robocasting method depends on the type of binders used and is well within the practice of those skilled in the art.

The sample using the (combined, binary) bentonite-silica binders and the (combined, binary) bentonite-aluminiumphosphate binders were slowly dried after robocasting in a controlled atmosphere at 80% relative humidity and 25° C. for 2 days. The dried structures were calcined at 550 ° C. for 3 hours using a heating rate of 1 ° C. per minute. The comparative sample using the single bentonite binder was also slowly dried after robocasting under the same conditions.

The (combined, binary) silica-aluminiumphosphate bound sample was rapidly dried during the robocasting process to avoid collapse of the structure. The comparative sample using the single silica binder as well as the comparative sample using the single aluminiumphosphate binder were also rapidly dried during the robocasting process.

A 3D-computer tomography (3D-CT) scan confirmed that there were no defects in the robocasted structures. Robocasted support materials are perfectly uniform throughout the structures.

FIG. 2 is an example of a 3D-CT scan image of robocasted binary binder bentonite/silica catalytic structure of the invention.

1B. Characterization of the Catalytic Structures

Rheological technique was used to determine the viscosity of the extrusion paste as a function of the shear rate (kinexus rheometer, Malvern Instruments, Worcestershire, United Kingdom).

Shear rates were varied between 0.01 and 1000 s$^{-1}$ ata temperature of 25° C.

Particle size distribution was measured using laser diffraction (Mastersizer X, Malvern Instruments, Worcestershire, United Kingdom) with a beam length of 10 mm.

The apparent specific surface area of the different catalysts was measured by $N_2$ sorption at −196° C. using the BET method (Autosorb-1, Quantachrome, Germany). Prior to $N_2$ sorption measurements, the samples were degassed for 16 h at 200° C. in order to remove all adsorbed water from the zeolite.

X-ray diffraction (XRD; X'pert PRO, Philips, Eindhoven, The Netherlands) was used to examine the phase and crystallinity of the self-supporting zeolites structures using a Cu—K$_\alpha$X-ray source ($\lambda$=1.54056 Å).

The surface and cross-sections of the catalyst were studied using a cold field emission scanning electron microscope (FEG-SEM) type JSM6340F (JEOL, Tokyo, Japan) at an acceleration voltage of 5 keV. To avoid charging under the electron beam during SEM, all samples were coated with a thin Pt(80)/Pd(20) (surfaces) or Au (cross-sections) layer (~1.5 nm), using a Cressington 208 HR (UK) and a Balzers Union SCD 040 (Balzers, Liechtenstein) high resolution sputter-coater, respectively. The thickness of the coating deposited onto the fiber was determined. $NH_3$-Temperature Programmed Desorption ($NH_3$-TPD) was performed on the pure zeolite powder and the coating to measure their acidity (Autosorb-iQ-Chemi, Quantachrome, Germany). Prior to TPD measurements, the samples were outgassed for 16 h at 200° C. under vacuum in order to remove all adsorbed water from the zeolite. After the pre-treatment the samples were saturated with ammonia at 100° C. The excess of ammonia was removed with a helium flow for 30 minutes. The temperature was raised from 100° C. to 750° C. at a rate of 10° C/min for the desorption of ammonia. The desorbed ammonia was detected using a thermal conductivity detector (TCD).

1C. Physicochemical Properties

Robocasted (macro)porous 3D (inherent) catalytic structures (having the same 1-1 structure) based on zeolite ZSM-5 as catalytic material are prepared as set out in section 1A. Structures having different combinations of inorganic binders were studied. Structures using only one single inorganic binder were analyzed as comparative examples.

The physical properties of binary binder robocasted structures of the invention (35 wt % binary binders vs. 65 wt % catalytic material) are given in Table 1.

TABLE 1 physical properties of different binary binder structures of the invention.

| Structure | BET surface area ($m^2/g$) | Micropore surface area ($m^2/g$) | Pore volume <50 nm ($cm^3/g$) | Macropore volume ($cm^3/g$) | Crush strength (MPa) |
|---|---|---|---|---|---|
| H-ZSM-5 (100% ZSM-5) | 428 | 379 | 0.159 | — | — |
| Bentonite/ AlPO$_4$ (65 wt % ZSM-5) | 219 | 140 | 0.111 | 0.404 | 1.54 |
| Bentonite/ Silica (65 wt % ZSM-5) | 301 | 242 | 0.282 | 0.572 | 0.66 |
| Silica/ AlPO$_4$ (65 wt % ZSM-5) | 177 | 126 | 0.051 | 0.445 | 0.57 |

The physical properties of single binder robocasted structures (35 wt % single binder vs. 65 wt % catalytic material) are given in Table 2 (comparative examples).

TABLE 2 physical properties of different single binder structures (comparative examples).

| Structure | BET surface area ($m^2/g$) | Micropore surface area ($m^2/g$) | Pore volume <50 nm ($cm^3/g$) | Macropore volume ($cm^3/g$) | Crush strength (MPa) |
|---|---|---|---|---|---|
| H-ZSM-5 (100% ZSM-5) | 428 | 379 | 0.159 | — | — |
| Bentonite (65 wt % ZSM-5) | 292 | 250 | 0.185 | 0.734 | 0.21 |
| Silica (65 wt % ZSM-5) | 305 | 234 | 0.266 | 0.412 | 0.22 |
| AlPO$_4$ (65 wt % ZSM-5) | 124 | 118 | 0.061 | 0.471 | 0.54 |

Nitrogen sorption measurements showed that the nature and the combinations of the binders has an influence on the specific surface area and pore volume of the final structure.

The micropore surface area of the single bentonite bound sample and single silica bound sample (Table 2) is not significantly different compared to 65% of the ZSM-5 zeolite. The single aluminiumphosphate bound sample however showed a decrease in micropore area due to the intrusion of the binder in to the pores of the zeolite. It was already suggested in literature (in Freiding et. al., Appl. Catal. A Gen. 328 (2007) 210) that after sintering, this binder can block the pores of the zeolite resulting into a loss of micropore area and micropore volume.

From Table 1, it can be seen that the nitrogen sorption measurements for the binary binder structures of the invention correspond with those of the single binder structures shown in Table 2.

The binary binder structures with an aluminiumphosphate binder (Table 1) show a decrease in specific surface compared with the single binder structure in Table 2, however the decrease in Table 1 is less than the single binder aluminiumphosphate structure as the aluminiumphosphate concentration is lower in the binary binder structure.

Hg-porosity measurements show an intermediate behavior of the porosity of the binary binder structures of the invention, compared to the single binder structures, according to the binders used.

The results of crush tests in Table 1 indicate that the combinational effect of different binders in the structures of the invention is beneficial for the mechanical strength of the final structure, even resulting in a synergic effect (combinational effect of the use of two different binders and their mutual interaction in the catalyst structures, being beneficial for the mechanical strength of the final structure). It is suggested that the bentonite binder allows the extrusion of a defect-free structure with good interconnection of the different layers, while the other binders form a strong network between the zeolite and bentonite binder during sintering.

The aluminiumphosphate binder in combination with the bentonite binder (Table 1) results in a structure with excellent mechanical strength, compared to the single binder systems (Table 2), high enough for industrial use. More particularly, the aluminiumphosphate/bentonite binary material shows three times higher strength than the single aluminiumphosphate binder sample and over seven times higher strength than the single bentonite sample. This synergic effect is also applicable for the bentonite/silica sample as this binary binder structure has three times higher mechanical strength than the single binder silica and bentonite structures.

The structure combining the silica binder with the aluminiumphosphate binder has sufficient mechanical strength (but does not result in superior mechanical strength compared to the single binder systems).

The results of mechanical tests for the single binder structures in Table 2 show that the structure with a single aluminiumphosphate binder has a higher mechanical strength than the structures with other single binders. However, the mechanical strength of the single binder structures (Table 2) is lower than the mechanical strength of the binary binder structures of the invention (Table 1).

The (value or degree of the) obtained mechanical strength of the structures of the invention, although improved with respect to the mechanical strength of the single binder structures in the art, depends on the type of structured catalyst used (i.e. on the type of the two inorganic binders used, the catalytic material used and the architecture of the catalytic structure). It will be apparent for those skilled in the art that the (value or degree of the) obtained mechanical strength has to be evaluated in view of the applications in which the structure is envisaged to be used.

Figure 3:
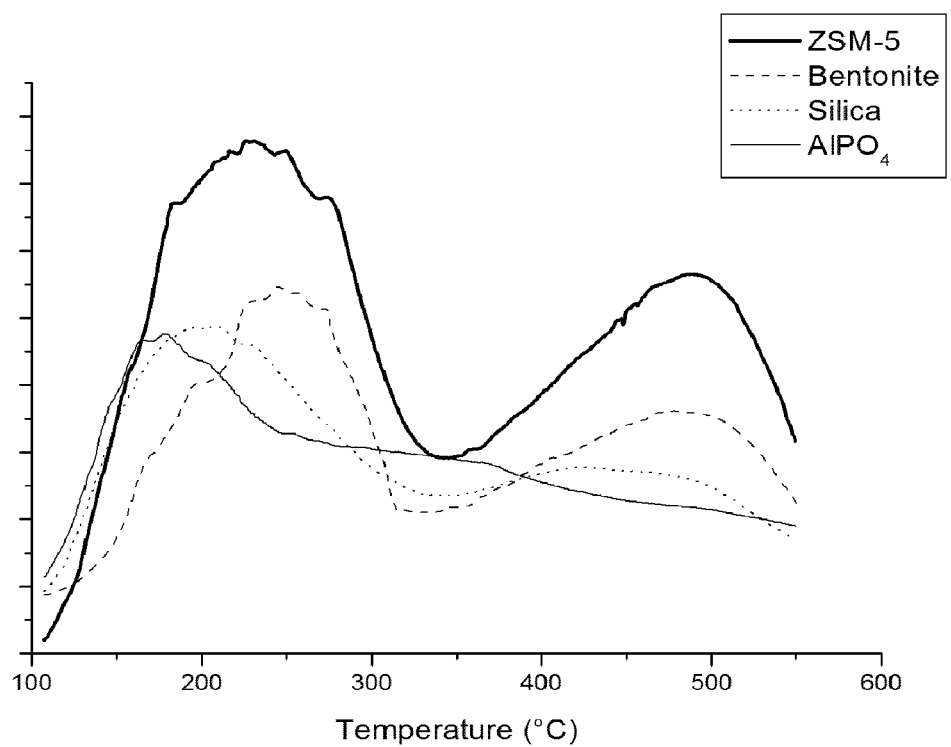
FIG. 3 represents $NH_3$-TPD profiles of robocasted single binder (Bentonite, Silica, or Aluminiumphosphate) bound zeolite structures based on zeolite ZSM-5 as catalytic material (comparative examples). The NH3-TPD profile of ZSM-5 is also shown.

NH$_3$-TPD profiles of the single binder bound zeolite structures shown in FIG. 3 indicate a difference in acidity depending on the single binder used in the formulation of the catalytic structure. The single bentonite binder has no impact on the acid sites of the zeolite whereas the structure with single silica binder shows a decrease in strong acids sites. The small amount of sodium ions present in the Ludox HS-40 silica binder neutralizes part of the acid sites present in the zeolite resulting in the lower acidity. The use of a single aluminiumphosphate binder decreases the acidity even more due to interaction of the phosphor with the acid sites of the zeolite.

Figure 4:
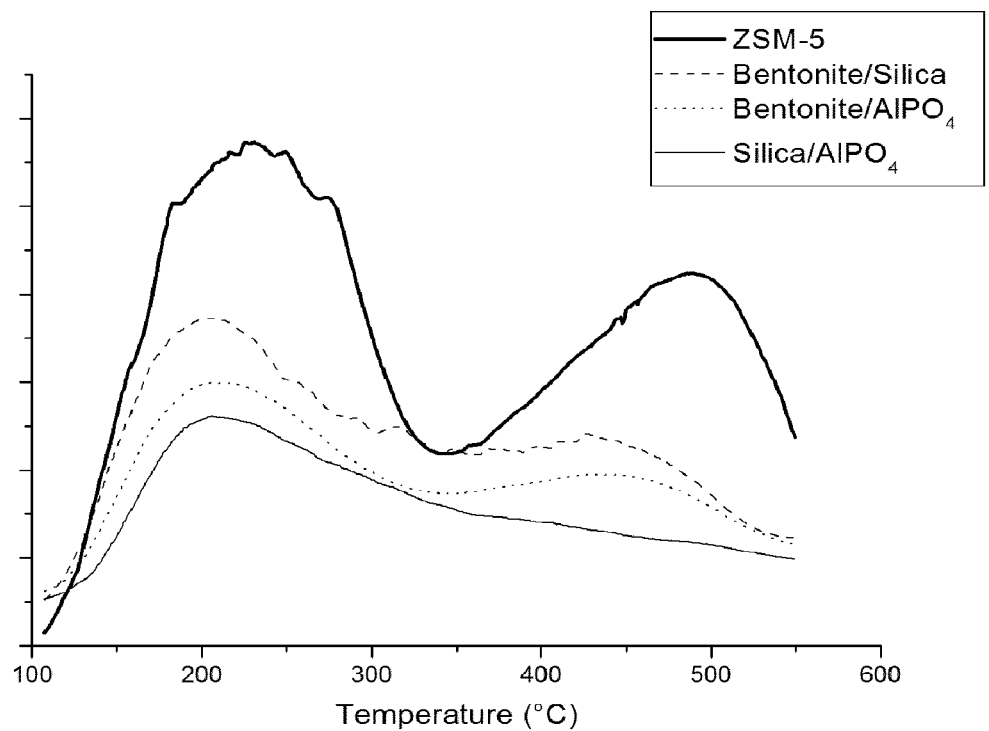
FIG. 4 represents $NH_3$-TPD profiles of robocasted binary binder (Bentonite/Silica, Silica/Aluminiumphosphate, or Bentonite/Aluminiumphosphate) bound zeolite structures of the invention based on zeolite ZSM-5 as catalytic material. The NH3-TPD profile of ZSM-5 is also shown.

The results of NH$_3$-TPD measurements of the binary binder bound zeolite structures of the invention are shown in FIG. 4. The use of silica results in a relatively small decrease in acidity while the use of aluminiumphosphate results in a larger decrease in acidity.

It is shown from the results in example 1 that the binders used in the formulation of robocasted structures have an impact on the behavior during the robocasting as well as on the physicochemical properties of the final structure.

The results above demonstrate that combining two types of inorganic binders in one catalyst structure, as described in the present invention, is beneficial to achieve desired properties in the final structure.

It is shown in example 1 that combining bentonite with inorganic binders such as aluminiumphosphate or silica, superior mechanical properties can be obtained compared to single binder catalyst structures (i.e. compared to prior art 3D catalytic structures).

The binary inorganic binders in the catalytic structures of the invention, as discussed in example 1, prove to have a significant impact on the specific surface area, porosity and acidity of the final component.

Example 2:

2A. Catalytic Results of Robocasted ZSM-5 Structures for Methanol-to-Olefins Reaction Robocasted (macro)porous 3D (inherent) catalytic structures (having the same 1-1 structure) based on zeolite ZSM-5 as catalytic material are prepared as set out in section 1A. Structures having different combinations of inorganic binders were studied. Structures using only one single inorganic binder were also analyzed as comparative examples.

Catalytic testing was performed in a fixed bed reactor with an inner diameter of 25 mm and a length of 300 mm at atmospheric pressure and temperatures of 450° C. The catalyst structures with a length of 25 mm were packed in thin layer of quartz wool and placed in the middle of the reactor. The reactor can be considered as quasi-adiabatic as the heat transfer coefficients of the quartz wool and alumina of the reactor are very low. The weight of catalyst for these samples was around 3.4 g. With a weight fraction of 65 percent for the zeolite, this results in around 2.21 g of zeolite in the reactor. The (pure) zeolite powder used for the comparison was pelletized and sieved (0.125-0.250 mm fraction). The pelletized particles were diluted with inert, sintered Al$_2$O$_3$ pellets and placed in the same reactor volume as the structured catalysts.

Nitrogen gas was co-fed (300 ml/min) and used as diluent for methanol (Merck, 99.9%). The feed rate of the methanol was controlled using a HPLC pump at a constant flow rate of 0.1 ml/min resulting in a weight hourly space velocity (WHSV) of 1.4 $g_{methanol}/g_{catalyst}/h$. Methanol and nitrogen were mixed in an isothermal reservoir at 200° C. in order to achieve a homogenous flow of methanol. This mixture was fed to the quasi-adiabatic reactor zone through heated lines. The reaction enthalpy for MTO is −4.6 kcal/mol (−0.54 kJ/$g_{MeOH}$). The theoretical fully adiabatic temperature rise in the reactor caused by the heat of reaction would be maximum 75° C. For the reference zeolite powder, the reaction was carried out at a weight hourly space velocity (WHSV) in the range of 4.56-36.46 h$^{-1}$. The product distribution has been analyzed with a gas chromatograph using a dual thermal conductivity detector and flame ionization detector (450-GC, Bruker, Bremen, Germany). After achieving equilibrium at each flow rate an isothermal period of 1 hour was kept and 4 gas measurements were performed. After each run the catalyst samples were regenerated by burning of the coke at 550° C. for 2 hours in a stream of air.

The robocasted samples were analyzed until deactivation of the samples occurred. In the data analysis, all $C_5$+ species are combined in one group. The selectivity was determined for each sample at 90% conversion.

The conversion of methanol was calculated by the following equation:

$$X_{MeOH} = 1 - \frac{C_{MeOH,outlet}}{C_{MeOH,inlet}} \quad (1)$$

The selectivity and yield of the different components was defined by the following equation:

$$S_i = \frac{C_i}{\sum_n C_n} y_i = S_i * X_{MeOH+DME} \quad (2)$$

with n representing all components in the product stream except methanol and dimethylether (DME).

As all robocasted structures have the same architecture (i.e. a 1-1 structure), the difference between the samples is related to the physicochemical differences originating from the different binders used.

Figure 5:
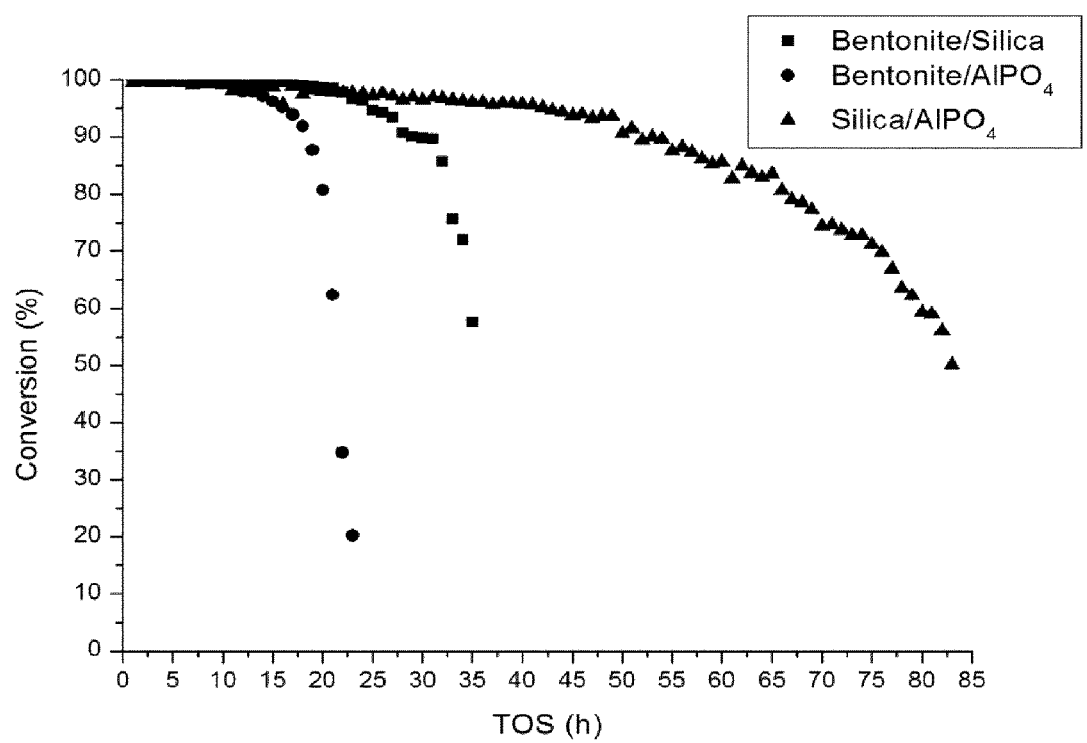
FIG. 5 shows the conversion of methanol to olefins as a function of time on stream for different binary binder catalysts of the invention (65 wt % ZSM-5/35 wt % binary binders, 450° C.).

The conversion of methanol to olefins as a function of time on stream (TOS) for the different binary binder catalysts of the invention (65 wt % ZSM-5/35 wt % binary binders, 450° C.) is shown in FIG. 5.

Figure 6:
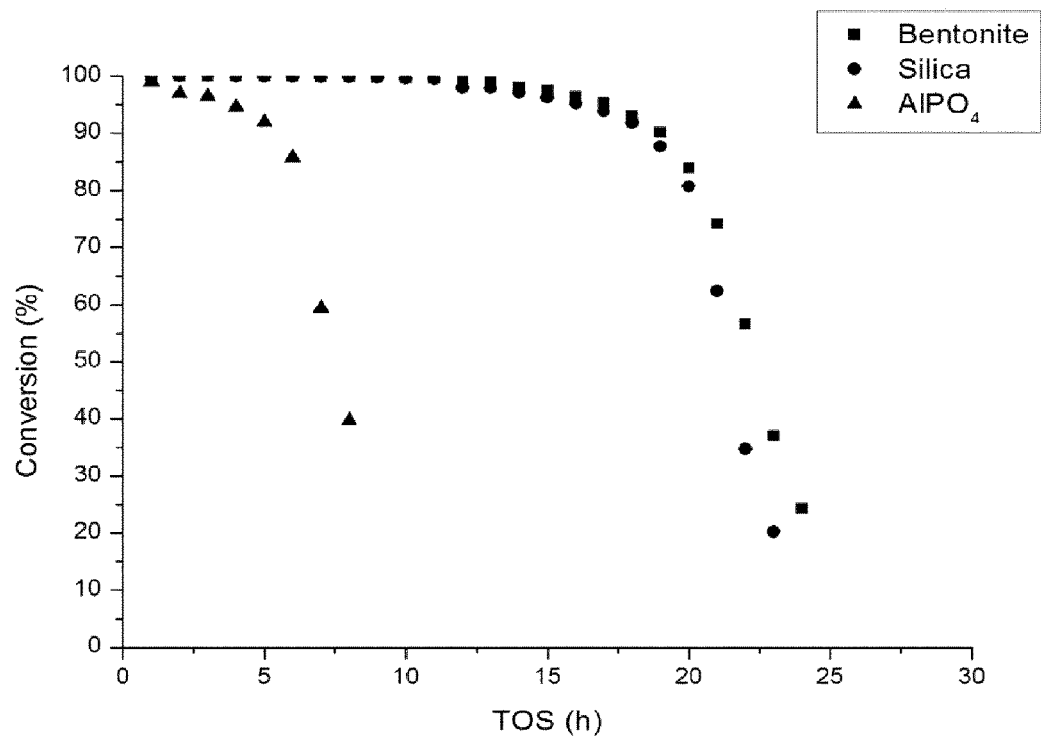
FIG. 6 shows the conversion of methanol to olefins as a function of time on stream for different single binder catalysts (65 wt % ZSM-5/35 wt % single binder, 450° C.) (comparative examples).

The conversion of methanol to olefins as a function of time on stream (TOS) for the different single binder catalysts (65 wt % ZSM-5/35 wt % single binder, 450° C.) is shown in FIG. 6 (comparative examples).

From these results in FIG. 6, it is clear that the single aluminiumphosphate binder has a major impact on the active sites of the zeolites. It was already suggested in literature (in Freiding et. al., Appl. Catal. A Gen. 328 (2007) 210) that the phosphate from the binder can diffuse into the pores and interact with the active site of ZSM-5 zeolite. Without being bound to theory, this could result in a lower acidity of the zeolite. Moreover, it has already been demonstrated by the results discussed in example 1 above, that the specific surface area and the acidity of the catalyst with an aluminiumphosphate binder declines. It is clear that at high concentrations of aluminiumphosphate the loss of active sites results in a major decrease of the activity of the catalyst. Although literature suggests that the coking rate of an aluminiumphosphate bound ZSM-5 is slower, the deactivation is fast, possibly due to the very limited number of remaining active sites. The single silica and single bentonite binder structures show similar stability of methanol conversion. Although the acidity of the single silica binder sample in slightly lower as for the single bentonite binder sample (as depicted in FIG. 3 discussed in example 1), the conversion of methanol in function of time on stream is similar. The results show that the stability mainly depends on the number and strength of the acid sites.

From the results in FIG. 5, it can be seen that the conversion of methanol as a function of time on stream for the binary binder systems of the invention shows an increase in stability compared to the single binder system (in FIG. 6). The bentonite/silica binary binder catalyst shows the highest stability, the stability being significantly higher than for the single silica system and single bentonite system (in FIG. 6), indicating a synergic effect (combinational effect of the use of two different binders and their mutual interaction in the catalyst structures, being beneficial for the stability of the final structure). Without being bound to theory, the reason for this improvement could be the better diffusion properties of the binary binder catalyst as the internal meso- and macroporosity of the silica/bentonite binder system is higher compared to the single silica binder system (the macropore volume for the silica/bentonite binder and single silica binder systems being 0.572 cm$^3$/g and 0.412 cm$^3$/g, respectively). Indeed, as the stability is affected by both the acidic properties and the diffusional properties of the catalyst, the slight decrease in strong acidity compared with the single bentonite sample in combination with improved diffusional properties, increases the stability. The combination of high macro- and mesopore volume using both binders together seems to improve the stability due to the better diffusional properties. The results confirm that the activity and coking rate are a function of acid site strength and density and porosity.

The silica/aluminiumphosphate binary binder sample and bentonite/aluminiumphosphate binary binder sample also show a major improvement in stability compared to the single binder aluminiumphosphate system (in FIG. 6).

Moreover, the NH$_3$-TPD measurement (cf. FIG. 4, example 1) clearly shows that the aluminiumphosphate concentration has a major impact on the acidity of the final catalyst, and as this concentration in the binary binder system is only half of that of the single binder system, the decrease in acidity is not so dramatically and more (weak acidic) active sites are conserved. The AlPO$_4$/SiO$_2$ sample with low strong acid site density can thus overcome the lower activity and result in higher stability due to a low coking rate. The silica/aluminiumphosphate binary binder sample shows a slower deactivation than the bentonite/aluminiumphosphate binary binder sample.

The selectivity of binary binder robocasted structures of the invention at 90% conversion (35 wt % binary binders vs. 65 wt % ZSM-5 catalytic material, 450° C.) are given in Table 3.

TABLE 3 selectivity (%) of binary binder robocasted structures of the invention at 90% conversion (35 wt % binary binders vs. 65 wt % ZSM-5 catalytic material, 450° C.).

| Sample | CH$_4$ | C$_2$H$_4$ | C$_3$H$_6$ | C$_4$H$_8$ | C$_2$-C$_4$ alkanes | C$_{5+}$ |
|---|---|---|---|---|---|---|
| ZSM-5 pellets | 6.4 | 13.6 | 12.2 | 23.8 | 27.5 | 16.5 |
| Bentonite/Silica | 8.9 | 17.7 | 22.7 | 16.6 | 8.0 | 26.1 |

TABLE 3-continued selectivity (%) of binary binder robocasted structures of the invention at 90% conversion (35 wt % binary binders vs. 65 wt % ZSM-5 catalytic material, 450° C.).

| Sample | CH$_4$ | C$_2$H$_4$ | C$_3$H$_6$ | C$_4$H$_8$ | C$_2$-C$_4$ alkanes | C$_{5+}$ |
|---|---|---|---|---|---|---|
| Bentonite/AlPO$_4$ | 4.4 | 19.1 | 33.0 | 13.9 | 7.6 | 22.0 |
| Silica/AlPO$_4$ | 2.6 | 12.0 | 42.7 | 12.7 | 0.3 | 29.7 |

The selectivity of the single binder robocasted structures at 90% conversion (35 wt % single binder vs. 65 wt % ZSM-5 catalytic material, 450° C.) are given in Table 4 (comparative examples).

TABLE 4 selectivity (%) of single binder robocasted structures at 90% conversion (35 wt % single binder vs. 65 wt % ZSM-5 catalytic material, 450° C.) (comparative examples).

| Sample | CH$_4$ | C$_2$H$_4$ | C$_3$H$_6$ | C$_4$H$_8$ | C$_2$-C$_4$ alkanes | C$_{5+}$ |
|---|---|---|---|---|---|---|
| ZSM-5 pellets | 6.4 | 13.6 | 12.2 | 23.8 | 27.5 | 16.5 |
| Bentonite | 12.4 | 17.5 | 25.0 | 14.6 | 6.9 | 23.6 |
| Silica | 9.8 | 20.7 | 14.1 | 17.7 | 10.3 | 27.4 |
| AlPO$_4$ | 1.3 | 12.4 | 42.2 | 11.4 | 1.9 | 30.8 |

Comparing the results from these tables, it can be seen that the selectivity of methanol to light olefins of the silica/aluminiumphosphate binary binder catalyst is very similar to that of the single binder aluminiumphosphate catalyst. However, the stability of this binary binder catalyst (cf. FIG. 5) is significantly higher than that of the single aluminiumphosphate binder sample (cf. FIG. 6). From the tables, similar results can be seen for the selectivity of the bentonite/silica binary binder catalyst versus the single binder bentonite catalyst (the stability of both structures being relatively high). To the contrary, although the selectivity of methanol to light olefins of the bentonite/aluminiumphosphate binary binder catalyst is similar compared to that of the single binder aluminiumphosphate catalyst, the stability of this binary binder catalyst (cf. FIG. 5) is lower than that of the single aluminiumphosphate binder sample (cf. FIG. 6).

More particularly, from the results it can be seen that the silica/aluminiumphosphate binary binder catalyst exhibits high selectivity towards propylene. The heavy alkenes make up a large part of the products, whereas the methane and alkane production is limited, due to major influence of the methylation and cracking cycles of alkenes on the selectivity and limited use of the (poly)methylbenzene methylation and dealkylation cycle. The selectivity of the bentonite/aluminiumphosphate catalyst towards light olefins is in between that of the single binder aluminiumphosphate and the bentonite catalysts. The characterization also confirms that it shows intermediate diffusion properties (porosity) (cf. Table 1, example 1) and acidity (cf. FIG. 4, example 1). Finally, the bentonite/silica containing sample shows similar behavior as the silica and bentonite binder catalysts, with methane and alkane production due to the use of the (poly)methylbenzene route as major pathway.

As the catalyst with the silica/aluminiumphosphate binder showed the highest yield of light olefins, different architectures of this catalyst were robocasted in order to further improve the catalyst. The results are discussed in the following section.

Figure 7:
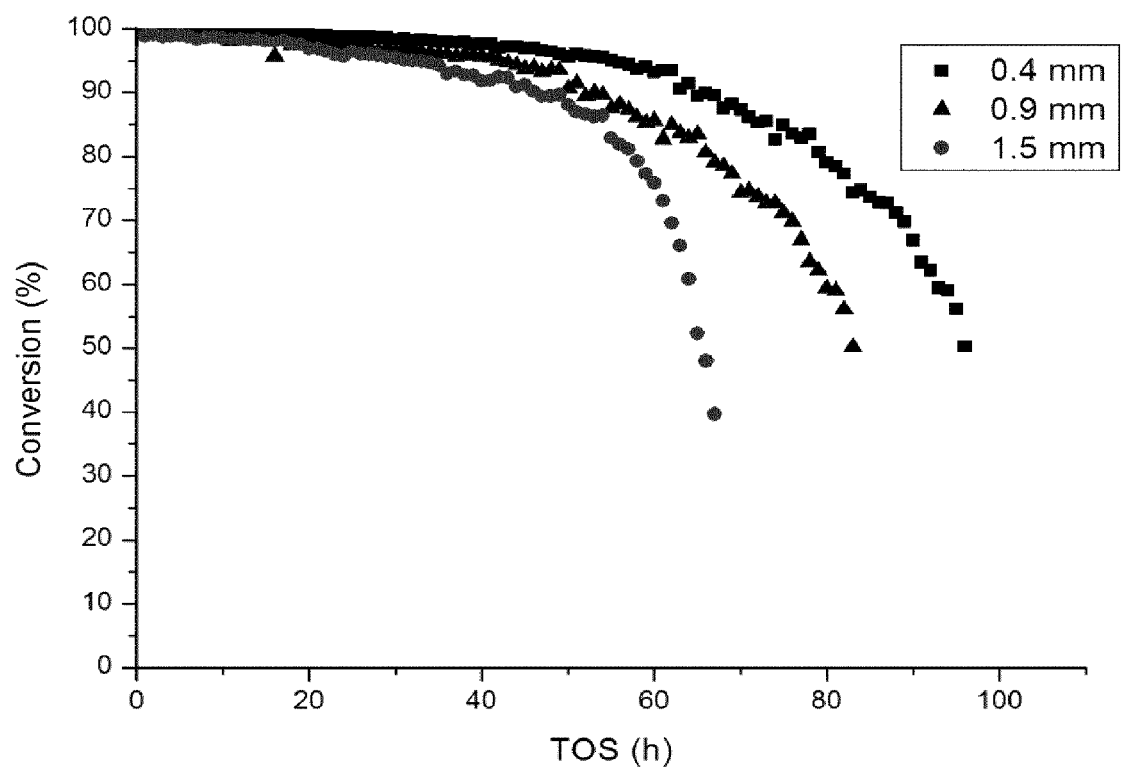
FIG. 7 shows the conversion of methanol as a function of time on stream for structures with different fiber diameter (65 wt % ZSM-5/35 wt % Silica/AlPO$_4$, 450 ° C.).

2B. Altering Architecture of the Catalytic Structure
2B. 1. Effect of Fiber Diameter In a first step the impact of the fiber diameter was evaluated. The results of catalytic testing of structures with fiber diameters of 400, 900 and 1500 µm are shown in FIG. 7 and Table 5.

TABLE 5 selectivity (%) of structures with different fiber diameter at 90% methanol conversion (65 wt % ZSM-5/35 wt % binder, 450° C.).

| Sample | $CH_4$ | $C_2H_4$ | $C_3H_6$ | $C_4H_8$ | $C_2$-$C_4$ alkanes | $C_{5+}$ |
|---|---|---|---|---|---|---|
| 1.5 mm | 2.1 | 12.2 | 41.2 | 13.2 | 3.2 | 28.1 |
| 0.9 mm | 1.8 | 9.3 | 42.3 | 14.5 | 3.0 | 29.1 |
| 0.4 mm | 2.1 | 12.1 | 40.9 | 13.9 | 3.9 | 27.1 |

The results suggest that there is a slight increase in stability with decreasing fiber diameter. This can be a result of the shorter diffusion path inside of the fibers of the structures. As the diameter of the struts increases, the reactants possibly diffuse too slow to reach the middle of the catalyst and the center of the fibers of the structure remain unused or less used. On the other hand, the diameter of the fibers influences the residence time in the fiber, which can also influence the cocking rate. However, if deactivated catalysts are analyzed, the center of the struts appear black, which points to coking in the center of the fiber. So it seems that the center part of the fibers of the structure take part in the reaction but the coke deposition on the catalyst can increase the diffusion limitation, so after certain time-on-stream the center of the fiber is less used than its outer shell.

From the results shown in Table 5, it can be seen that the selectivity towards propylene and light olefins does not change significantly with decreasing fiber diameter. This proves that there is no difference in reaction mechanism in the samples with different fiber diameter. Without wishing to be bound by theory, it is believed that the difference in deactivation is more probably due to a difference in loss of surface area.

The results of the samples with different fiber diameter suggest that there are no real mass or heat transfer limitations inside the fiber of the structure in the beginning of the reaction. As deactivation by coking occurs upon longer time-on-stream, channels of the zeolite get blocked and some channels seem longer accessible if the fiber diameter is smaller. This effect, caused by the increased outer surface of the struts, slightly postpones the complete deactivation of the catalyst.

2B. 2. Effect of Porosity

Figure 8:
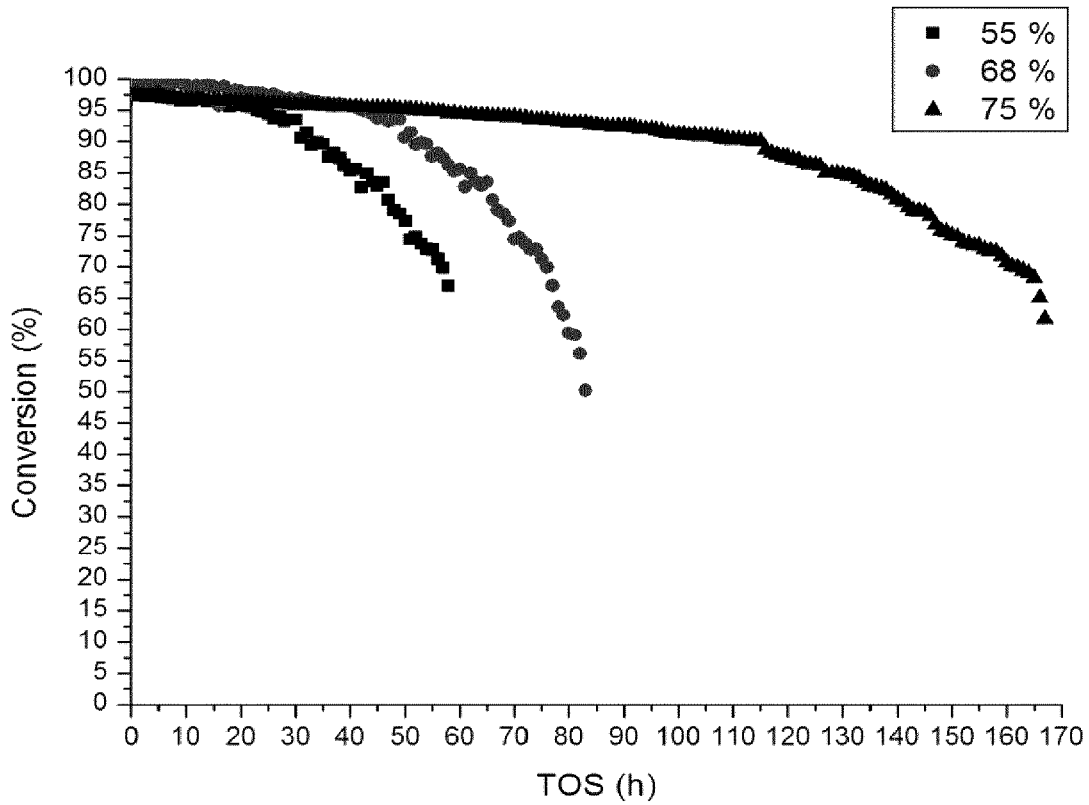
FIG. 8 shows the conversion of methanol as a function of time on stream for structures with different porosity (65 wt % ZSM-5/35 wt % Silica/AlPO$_4$, 450° C.).

The results of time-on-stream experiments for the methanol-to-olefins (MTO) reaction with catalytic structures that differ in macroporosity is shown in FIG. 8 and Table 6).

TABLE 6 selectivity (%) of structures with different porosity at 90% methanol conversion (65 wt % ZSM-5/35 wt % binder, 450° C.).

| Sample | $CH_4$ | $C_2H_4$ | $C_3H_6$ | $C_4H_8$ | $C_2$-$C_4$ alkanes | $C_{5+}$ |
|---|---|---|---|---|---|---|
| 75% | 1.4 | 9.4 | 43.1 | 14.4 | 2.1 | 29.5 |
| 68% | 1.8 | 9.3 | 42.3 | 14.5 | 3.0 | 29.1 |
| 55% | 1.5 | 14.1 | 41.7 | 15 | 4.4 | 23.3 |

At higher porosity (75%), the stability increases significantly compared to the standard catalyst with 68% porosity. The sample with 55% porosity in the structure showed a reduced stability.

As the difference in porosity is solely a result of difference in open frontal area, the gas velocity through the structure was higher or lower according to the higher and lower porosity of the structure. In this way, also the mass and heat transfer properties were affected. The lower bulk mass and heat transfer and larger pores in direction of the flow can result in a lower concentration of methanol on the catalyst surface at the entrance of the reactor. Hence, less heat will be released locally and thus the generation of heat from the exothermic MTO reaction could be spread out over a longer length of the catalyst bed for the same amount of catalysts. The bed is thus more dispersed. In this way, coking can be reduced.

It should be noted that the initial activity in the bed with higher porosity is lower as in the start-up phase of the reaction it took longer time to reach full conversion compared to the samples with lower porosity (45 min vs 15 min). Furthermore, 100% conversion was never reached in the catalyst bed with high porosity. Moreover, if the reactor is not fully adiabatic and some heat transfer occurs via the surface of the reactor, the longer bed can exchange more heat with the outside. Thus, the temperature rise in the catalyst bed due to the exothermic nature of the reaction could be lower compared to the structures with lower porosity.

From the results shown in Table 6, it can be seen that there is no clear difference in propylene selectivity between the samples with different porosity. The ethylene yield on the other hand is higher for the structure with the low porosity. As the temperature inside the catalyst bed depends on the amount of methanol converted per volume of catalyst, the high density structure can be expected to have a higher temperature inside the fibers, increasing the cracking rate. The higher temperature inside of the reactor can have a significant impact on the selectivity as well.

The results show that higher temperature promotes ethylene selectivity and lowers heavy olefin selectivity. The cracking rate of the heavier alkenes increases, resulting in the higher ethylene yield and lower yield of $C_5$-$C_7$ alkenes. On the other hand, the increased pressure drop in the structure with lowest porosity could have an impact on the selectivity.

2B. 3. Effect of Fiber Stacking

Different architectures of the silica/aluminiumphosphate binary binder catalyst of the invention were robocasted. The architecture of the channels in the structures and thus the diffusion path and tortuosity is changed by changing the stacking of the different layers during the robocasting process. More particularly, 3DFD structures with 1-1 and 1-3 stacking were manufactured using a 0.9 mm diameter nozzle and a programmed inter fiber distance of 1.1 mm.

Figure 9:
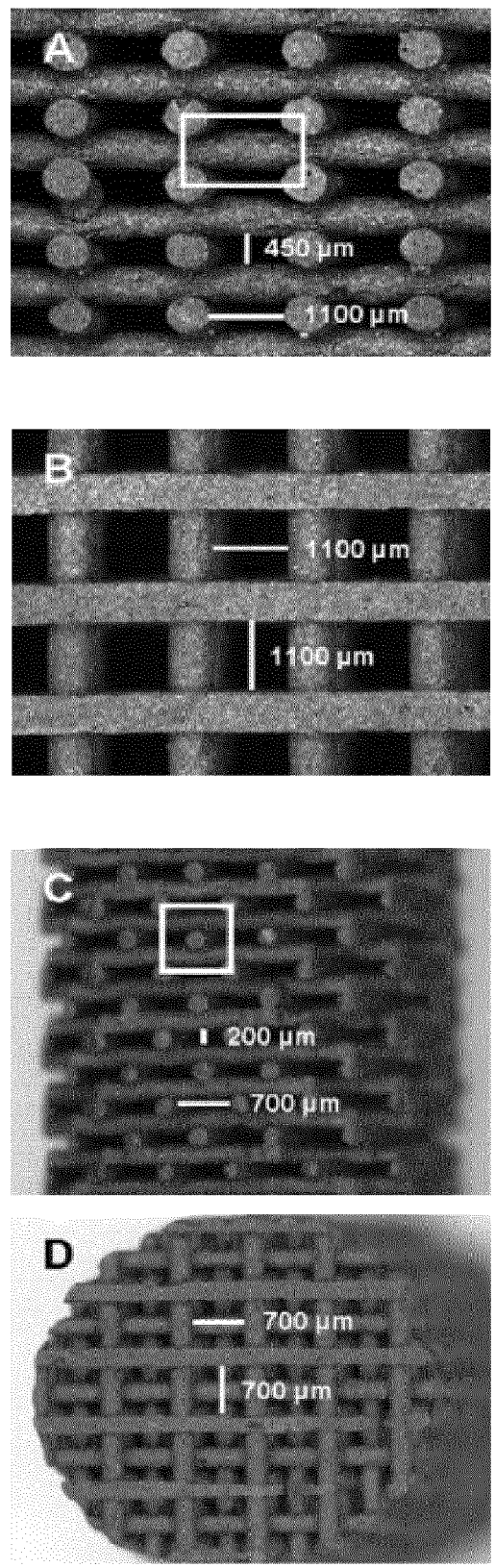
FIG. 9 shows optical microscope images of a 1-1 3DFD tetragonal structure (FIGS. 9A and 9B); a 1-3 3DFD face-centered structure (FIGS. 9C and 9D); with side and top view of the structures shown in FIGS. 9A, 9C and FIGS. 9B, 9D, respectively.

The 1-1 stacked 3DFD structure has straight channels in the direction of the flow (1.1×1.1 mm) in combination with smaller radial channels (1.1×0.45 mm) in two directions. Structured supports with straight channels have very low tortuosity in the flow and help overcome back mixing and a broad contact time distribution of the reagents. The fibers of the 1-1 structure show a tetragonal symmetry. Optical microscope images of such a tetragonal structure (1-1 3DFD structure) are shown in FIG. 9A (side view) and FIG. 9B (top view).

The 1-3 stacked 3DFD structure has 'zigzag' channels (i.e. a tortuous path) in the direction of the flow (1.1×1.1 mm) and smaller straight channels (1.1×0.45 mm) in two radial directions. The 1-3 stacked structure, having tortuous channels in flow direction, has a face centered symmetry. Optical microscope images of such a face-centered structure (1-3 3DFD structure) are shown in FIG. 9C (side view) and FIG. 9D (top view). The materials used for the 1-3 stacked 3DFD structure, however, have different sizes than indicated in FIGS. 9C and 9D. The applied dimensions for the catalytic tests for this structure are 1100 µm and 450 µm instead of the indicated 700 µm and 200 µm in said figures, respectively.

In order to evaluate the difference between the structured catalysts and a packed bed, also pellets with the same zeolite-binder composition as the robocasted structures were produced by extrusion. An equal mass of pellets with a diameter of 2 mm and a length of 15 mm were loaded in the reactor for catalytic testing.

Figure 10:
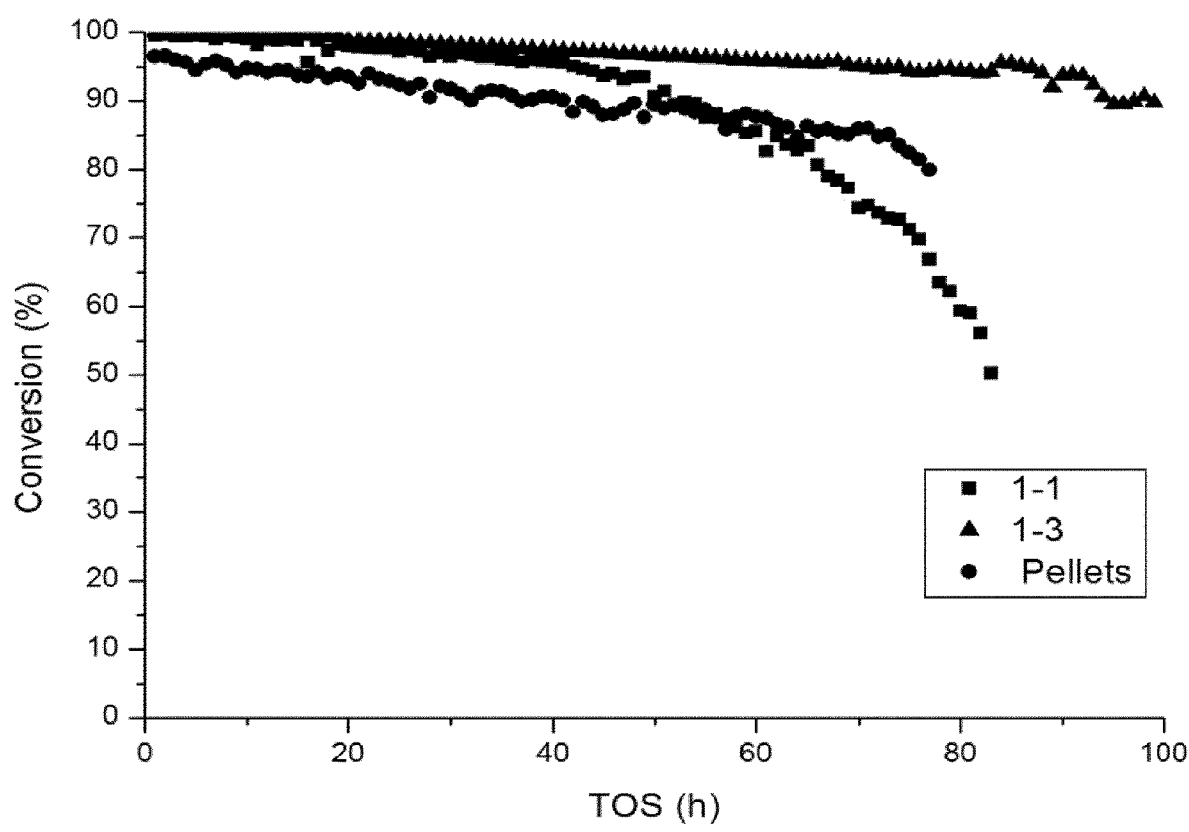
FIG. 10 shows the conversion of methanol to olefins as a function of time on stream for binary binder silica/aluminiumphosphate ZSM-5 catalysts of the invention with different architectures (65 wt % ZSM-5/35 wt % binary binders, 450° C.).

The conversion of methanol to olefins as a function of time on stream for binary binder silica/aluminiumphosphate ZSM-5 catalysts of the invention with the different architectures (65 wt % ZSM-5/35 wt % binary binders, 450° C.) is shown in FIG. 10.

The selectivity of the binary binder Silica/AlPO$_4$ catalyst of the invention with different architectures at 90% conversion (35 wt % binary binders vs. 65 wt % ZSM-5 catalytic material, 450° C.) are given in Table 7.

TABLE 7 selectivity (%) of binary binder Silica/AlPO$_4$ catalyst of the invention with different architectures at 90% conversion (65 wt % ZSM-5/35 wt % binary binders, 450° C.).

| Sample | $CH_4$ | $C_2H_4$ | $C_3H_6$ | $C_4H_8$ | $C_2$-$C_4$ alkanes | $C_{5+}$ |
|---|---|---|---|---|---|---|
| Silica/AlPO$_4$ 1-1 straight channels | 2.6 | 12.0 | 42.7 | 12.7 | 0.3 | 29.7 |
| Silica/AlPO$_4$ pellets | 0.7 | 5.8 | 47.1 | 13.9 | 0.9 | 31.6 |
| Silica/AlPO4 1-3 zigzag channels | 1.2 | 7.4 | 47.2 | 14.3 | 1.9 | 28.0 |

The catalytic results in FIG. 10 show a significant improvement in stability by using a packed bed of the catalyst or a 1-3 architecture with 68% porosity (structure with zigzag channels in direction of the flow) compared to the structure with straight channels. However the initial conversion of the 1-1 structure with straight channels is higher, the deactivation is faster.

From Table 7 it can be seen that the selectivity towards light olefins of the packed bed and the zigzag 1-3 channeled sample is also significantly better than for the structure with straight channels. The structured catalyst with the zigzag channel performs slightly better than the packed bed with an overall $C_2$-$O_4$ olefin selectivity of almost 69%.

The results suggest that the turbulence of the flow, created when using a packed bed or structure with zigzag channels, is more efficiently removing the heat of the reaction from the structure, resulting in slower deactivation by coking and less side reactions (the catalyst structures thus showing improved selectivity). Indeed, inefficient heat removal or transfer can give rise to the formation of hot spots throughout the structure. In such a hot spot, the heat builds up due to the exothermic nature of the reaction leading to a faster, less controlled reaction and production of more heat. This effect induces a loss in selectivity of the reaction as well as rapid coke formation and deactivation. By introducing radial convection, obtained by using a 1-3 3D designed structure that enforces tortuosity in the fluid flow, the radial heat transfer properties of the catalyst are improved. As such, the reaction is more controlled and uniform, hence avoiding the formation of hot spots and leading to higher efficiency of mixing of the flow inside the structure which in turn results in lower and possibly different cokes. Due to the higher mixing efficiency the heat of the exothermic reaction can thus be better removed, resulting in a lower temperature at the surface of the 1-3 structured catalyst as well.

Although similar in catalytic selectivity and stability, the packed bed still has a major drawback in bulk mass diffusion and higher pressure drop compared to the 1-3 structured catalyst (the bulk mass and heat transfer properties being better in the structure with zigzag channels and high tortuosity in the flow compared to the 1-1 structure). The 1-3 structures has shown to be in the same range as foams for pressure drop, still one order of magnitude lower than the pressure drop in a packed bed at equal external surface area. The structure with 1-1 stacking showed a pressure drop still around 3.5 times lower than the structure with 1-3 stacking.

The impact of different binders of ZSM-5 on the stability and selectivity of the conversion of methanol to olefins was shown in example 2.

It is shown that due to the decrease in strong acidity (and specific surface area) when using an aluminiumphosphate binder, the selectivity of the reaction (i.e. selectivity to light oleofins) was improved. However, if the aluminiumphosphate was used as single binder, the stability of the catalyst was low probably due to a major decrease in active sites.

The results in example 2 demonstrate that the binary binder system of the invention using aluminiumphosphate in combination with a silica binder significantly improved the lifetime of the catalyst, while the superior selectivity towards light olefins was not affected. This indicates a combinational (synergic) effect of the use of two different binders and their mutual interaction in the catalytic structure, being beneficial for the stability of the final structure and for its selectivity towards light olefins.

The degree of obtained stability and selectivity of the catalytic structures of the invention depends on the type of structured catalyst used, i.e. on the type of the two inorganic binders used, the catalytic material used and the architecture of the catalytic structure (and is evaluated in view of the applications in which the structure is used).

By altering the architecture of the catalyst comprising two (different types of) inorganic binders, even better lifetime and selectivity of the catalyst can be obtained. The stability of the catalyst improved with decreasing fiber diameter and increasing porosity. The selectivity on the other hand, was only slightly affected by changes in structural characteristics (fiber diameter and porosity). The silica/aluminiumphosphate ZSM-5 catalytic structure with 1-3 architecture (zigzag channels in the direction of the flow) exhibited an improved stability and selectivity compared to the 1-1 structure with straight channels due to tortuosity in the flow (i.e. due to the better mass and heat transfer properties of this type of structured catalyst).

It has thus been shown that changes in architecture of the catalyst has a major impact on its catalytic properties. Hence, the catalyst architecture can even be further tuned in function of the application under consideration. More particularly, the porosity, the wall thickness and the architecture of the channels can be altered independently of changes in catalyst properties and addition of promoting binders. More complex designs are also possible: e.g. gradient structures with more or less catalyst at the wall or center, or at the top or bottom of the catalyst bed; or rotating structures with helix like channels (i.e. the subsequent layers being turned by a few degrees compared to the previous one) or shifted helix like channels for even better mixing efficiency.

Taking MTO reactions as an example, a gradient structure with high porosity in the beginning of the catalyst bed followed by an increase in density of the catalyst towards the end of the catalyst bed could be beneficial. In this way, the heat of the reaction is better dissipated over the length of the catalyst bed. Indeed, the chance of a methanol molecule of hitting the catalyst is low in the beginning of the catalyst bed as the concentration of methanol is still high at that moment of the MTO reaction. As the concentration of methanol decreases, the chance of a methanol hitting the catalyst increases with the density increase, resulting in a better spread of the heat of reaction.

Rotating structures, for example, can have high mixing behavior at relatively low pressure drops.

Furthermore, the amount of binder and ratio of different binders can be altered according to the application in which the structure is used. The use of the robocasting technique and careful selection of suspension compositions can be of great advantage in process intensification by optimization of the catalytic systems.

From the description and examples 1 and 2 above, it follows that the present invention thus provides improved catalytic compositions and catalytic structures made thereof, which overcome the disadvantages of prior art catalytic compositions and structures.

The present invention provides (inherent) catalytic structures, having improved mechanical and physicochemical properties (compared to prior art catalytic structures).

The (inherent) catalytic structures of the present invention also have improved catalytic properties (compared to prior art catalytic structures).

More particularly, the effectiveness of the active catalytic component in the structures of the present invention has improved, compared to prior art catalytic structures.

The use of rapid prototyping techniques such as three dimensional fiber deposition allows manufacturing of periodic catalytic supports with different architectures, said catalysts being highly uniform throughout the structures. More particularly, by using 3D-printing techniques, advantageously three dimensional fiber deposition technique, the architecture of the catalyst can be optimized leading to improved mass and heat transfer properties, in order to improve the activity, selectivity and stability of the catalyst. The stacking of the fibers have a major impact on the mass and heat transfer properties and pressure drop of the final catalyst. It has been shown that by changing the stacking of the layers of the structure, highly periodic structures, introducing turbulent flow, can be created. Aspects related to the tortuosity (mixing, contact time, etc.) and ease of diffusion in the total available catalyst surface clearly influence performance in activity, selectivity and stability.

Furthermore, the use of the robocasting technique for manufacturing of self-supporting catalysts improves the effectiveness of the active component in the structure and increases the loading of active material per reactor volume compared to for example coated structured supports known in the art. Moreover, direct synthesis of an inherent catalytic structure requires less process steps during the manufacturing than manufacturing of a support followed by one or multiple coatings to achieve sufficient loading of the catalyst.

Even though the above examples have been illustrated using a robocasting manufacturing method for obtaining the catalytic structures of the invention, it will be clear to those skilled in the art that also other types of colloidal ceramic shaping techniques (such as conventional extrusion, foam manufacturing, washcoating, or the like) can be applied to obtain the catalytic structures of the present invention.

The invention claimed is:

1. A method for performing methanol-to-olefins reactions, comprising:
    building a bulk catalytic structure, comprising:
        shaping a composition comprising a ceramic material to obtain a green structure, wherein said ceramic material comprises a catalytic material and a first inorganic binder and a second inorganic binder, the shaping comprising preparing a suspension, slurry or paste of the composition and extruding the suspension, slurry or paste as fibers by three-dimensional fiber deposition to obtain the green structure, wherein the fibers are spaced apart to form a porous layered network;
        the total amount of the first and second inorganic binders in the ceramic material comprising between 10 wt % and 50 wt % by total solid weight of the formed catalytic structure;
        wherein the first inorganic binder is a clay material and the second inorganic binder is selected from: colloidal silica, colloidal alumina, colloidal zirconia, colloidal yttrium oxide, or colloidal tin oxide; or the first inorganic binder is selected from: colloidal silica, colloidal alumina, colloidal zirconia, colloidal yttrium oxide and the second inorganic binder is an inorganic thermohardening compound;
        drying and calcining the green structure to obtain the bulk catalytic structure, wherein the structure is monolithic and comprises first channels having a length extending in a flow direction and second channels having a length extending in a radial direction, wherein the first channels and the second channels are fluidly connected; and
    using the bulk catalytic structure as a catalyst in the methanol-to-olefins reactions.

2. The method according to claim 1, wherein the fibers extend alongside the first and the second channels.

3. The method according to claim 1, wherein the fibers have a diameter between 0.1 mm and 2 mm.

4. The method according to claim 1, wherein the bulk catalytic structure has a macroporous volume in the range between 0.25 cm$^3$/g and 1.0 cm$^3$/g.

5. The method according to claim 4, wherein the macroporous volume is between 0.35 cm$^3$/g and 0.75 cm$^3$/g.

6. The method according to claim 1, wherein the bulk catalytic structure has a pressure drop smaller than or equal to 0.3 bar/m at a superficial gas velocity of 0.04 m/s in a flow of nitrogen at about 303 K.

7. The method according to claim 6, wherein the pressure drop is smaller than or equal to 0.2 bar/m.

8. The method according to claim 6, wherein the pressure drop is smaller than or equal to 0.1 bar/m.

9. The method according to claim 1, wherein the clay material is bentonite.

10. The method according to claim 1, wherein the inorganic thermohardening compound is aluminumphosphate.

11. A method for performing catalytic applications, comprising:
    building a bulk catalytic structure, comprising:
        shaping a composition comprising a ceramic material to obtain a green structure, wherein said ceramic material comprises a catalytic material and a first organic binder and a second inorganic binder, the shaping comprising preparing a suspension, slurry or paste of the composition and extruding the suspension, slurry or paste as fibers by three-dimensional fiber deposition to obtain the green structure, wherein the fibers are spaced apart to form a porous layered network;

the total amount of the first and second inorganic binders in the ceramic material comprising between 10 wt % and 50 wt % by total solid weight of the formed catalytic structure;

wherein the first inorganic binder is a clay material and the second inorganic binder is selected from: colloidal silica, colloidal alumina, colloidal zirconia, colloidal yttrium oxide, or colloidal tin oxide; or the first inorganic binder is selected from: colloidal silica, colloidal alumina, colloidal zirconia, colloidal yttrium oxide and the second inorganic binder is an inorganic thermohardening compound;

drying and calcining the green structure to obtain the bulk catalytic structure, wherein the structure is monolithic and comprises first channels having a length extending in a flow direction and second channels having a length extending in a radial direction, wherein the first channels and the second channels are fluidly connected; and using the bulk catalytic structure for catalytic applications.

12. A method for performing ion-exchange applications, comprising:

building a bulk catalytic structure, comprising:

shaping a composition comprising a ceramic material to obtain a green structure, wherein said ceramic material comprises a catalytic material and a first organic binder and a second inorganic binder, the shaping comprising preparing a suspension, slurry or paste of the composition and extruding the suspension, slurry or paste as fibers by three-dimensional fiber deposition to obtain the green structure, wherein the fibers are spaced apart to form a porous layered network;

the total amount of the first and second inorganic binders in the ceramic material comprising between 10 wt % and 50 wt % by total solid weight of the formed catalytic structure;

wherein the first inorganic binder is a clay material and the second inorganic binder is selected from: colloidal silica, colloidal alumina, colloidal zirconia, colloidal yttrium oxide, or colloidal tin oxide; or the first inorganic binder is selected from: colloidal silica, colloidal alumina, colloidal zirconia, colloidal yttrium oxide and the second inorganic binder is an inorganic thermohardening compound;

drying and calcining the green structure to obtain the bulk catalytic structure, wherein the structure is monolithic and comprises first channels having a length extending in a flow direction and second channels having a length extending in a radial direction, wherein the first channels and the second channels are fluidly connected; and using the bulk catalytic structure for ion exchange applications.

13. The method according to claim 12, wherein the fibers have a diameter between 0.1 mm and 2 mm.

14. The method according to claim 12, wherein the bulk catalytic structure has a macroporous volume in the range between 0.25 $cm^3$/g and 1.0 $cm^3$/g.

15. The method according to claim 12, wherein the bulk catalytic structure has a pressure drop smaller than or equal to 0.3 bar/m at a superficial gas velocity of 0.04 m/s in a flow of nitrogen at about 303 K.

16. The method according to claim 12, wherein the clay material is bentonite.

17. The method according to claim 12, wherein the inorganic thermohardening compound is aluminumphosphate.

\* \* \* \* \*